(12) United States Patent
Kanner

(10) Patent No.: US 6,506,210 B1
(45) Date of Patent: Jan. 14, 2003

(54) WOUND SITE MANAGEMENT AND WOUND CLOSURE DEVICE

(75) Inventor: Glenn Kanner, Plymouth, MA (US)

(73) Assignee: AngioLink Corporation, Stoughton, MA (US)

( * ) Notice: Subject to any disclaimer, the term of this patent is extended or adjusted under 35 U.S.C. 154(b) by 29 days.

(21) Appl. No.: 09/658,787

(22) Filed: Sep. 11, 2000

(51) Int. Cl.[7] ............................................... A61B 17/04
(52) U.S. Cl. .................... 606/213; 606/216; 227/179.1; 227/181.1
(58) Field of Search ........................... 227/179.1, 181.1, 227/175.1

(56) References Cited

U.S. PATENT DOCUMENTS

| | | | |
|---|---|---|---|
| 264,290 A | 9/1882 | Hogan | |
| 5,122,156 A | 6/1992 | Granger et al. | 606/219 |
| 5,234,447 A | 8/1993 | Kaster et al. | 606/153 |
| 5,478,354 A | 12/1995 | Tovey et al. | 606/219 |
| 5,797,933 A | * 8/1998 | Snow et al. | 606/151 |
| 6,004,341 A | 12/1999 | Zhu et al. | 606/198 |

* cited by examiner

Primary Examiner—Gary Jackson
(74) Attorney, Agent, or Firm—Grossman, Tucker, Perreault & Pfleger, PLLC

(57) ABSTRACT

A staple and stapler and introducer are disclosed for closing a wound and for wound site management. The staple is deformable, and includes a plurality of tissue-piercing prongs which are expanded outwardly, inserted into tissue and collapsed inwardly to close the wound. The stapler includes a plurality of mechanisms to deform the staple into various positions. An introducer is provided that includes a plurality of spaced-apart wire guides for securing and centering the wound opening during a medical procedure, and during closure of the wound.

8 Claims, 24 Drawing Sheets

$F_1$

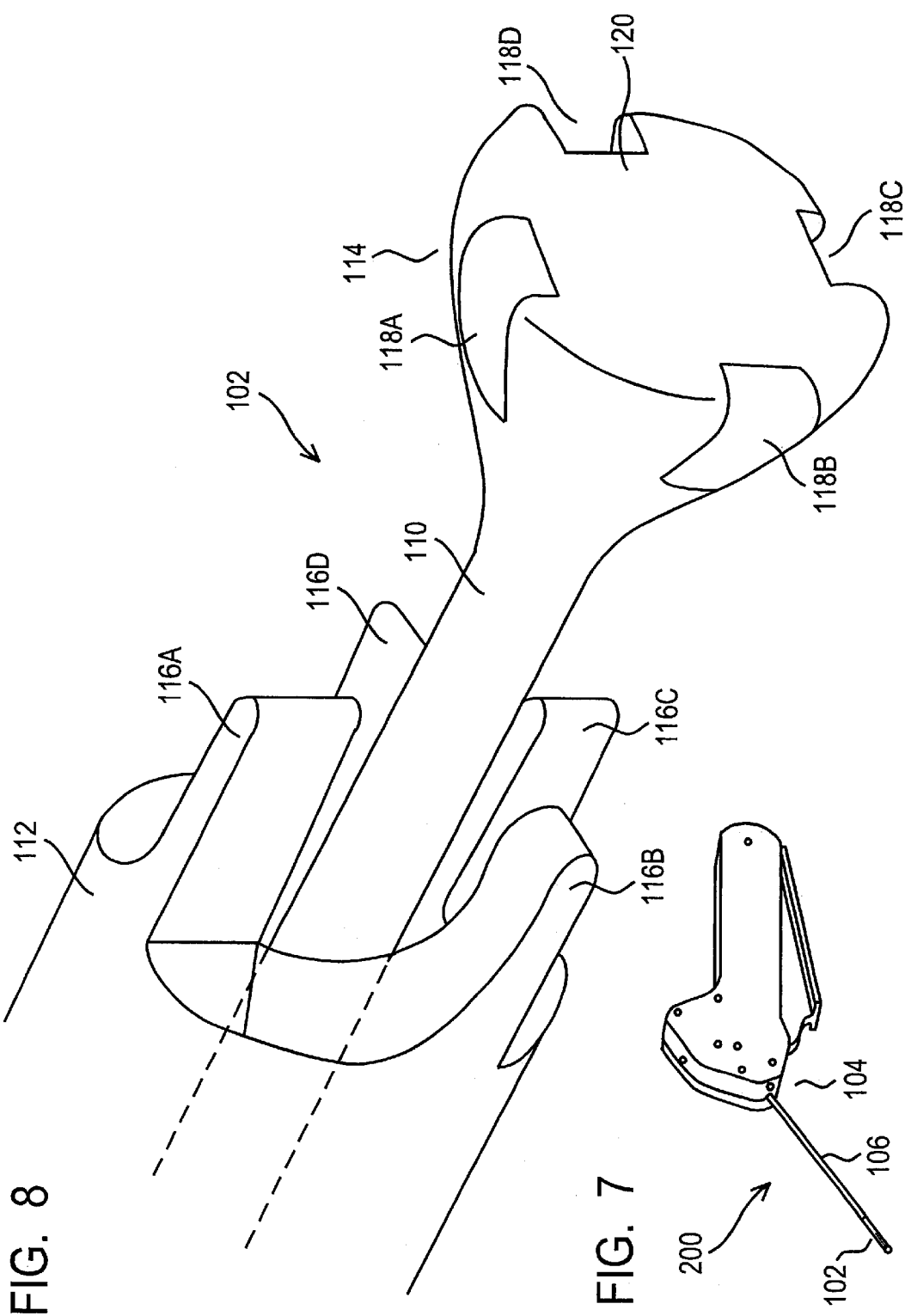

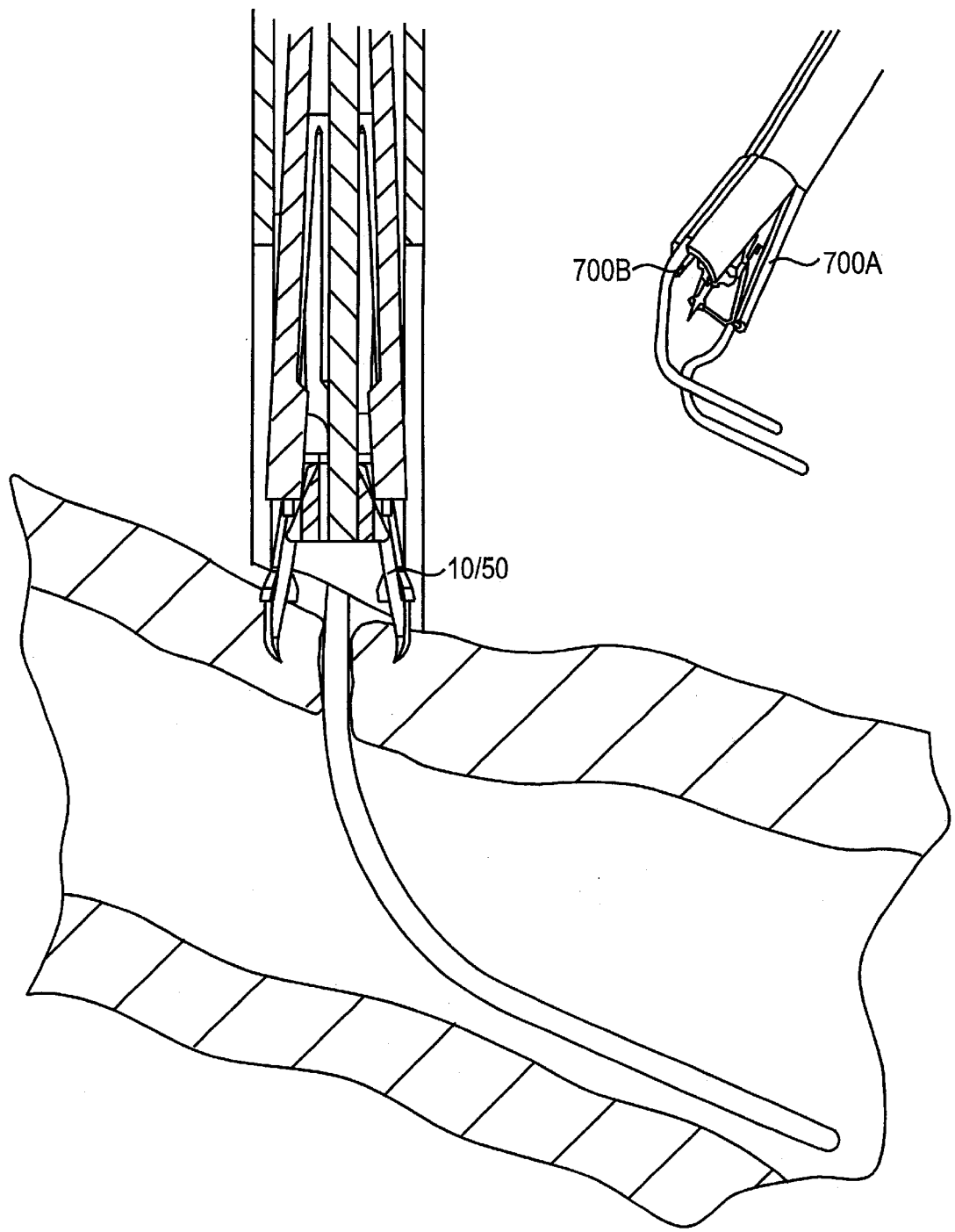

WOUND SITE MANAGEMENT AND WOUND CLOSURE DEVICE

BACKGROUND OF THE INVENTION

1. Field of the Invention

The present invention relates to a wound site management and wound closure device and method, for use during and after an invasive medical procedure. More specifically, the present invention relates to a staple and stapling device for closing a puncture made in the wall of an artery or vein during a medical procedure. The puncture may be the result of a catheter-based intervention, although any puncture is contemplated, accidental or intentional. The present invention has particular utility for use in and around the femoral, radial, and brachial arteries after coronary/cardiac procedures. Other utilities include soft-tissue anchoring, tendon and artery joining, meniscal repair, thoracic lung closure, heart repair, endoscopic procedures, esophageal repair, laparoscopy, skin/epidermal wound closure and general tissue closure.

2. Description of Related Art

Catheters/catheterization procedures are well known, and typically involve insertions through the femoral artery for diagnosis or to treat cardiovascular and /or peripheral vascular diseases. After a diagnostic or interventional catheterization, the puncture formed by the catheter must be closed. The puncture opening in the artery typically ranges from 5F for a diagnostic procedure to 6–10F for an interventional procedure. Traditionally, intense pressure has been applied to the puncture site for at least 30–45 minutes after removal of the catheter. Other approaches include a thrombotic or collagen plug, and/or other suturing methodology for sealing the puncture. Patients who have had a femoral puncture are then required to remain at bed rest, essentially motionless and often with a heavy sandbag placed on their upper legs, for several hours to ensure that the bleeding has stopped. This traditional method of hemostasis following femoral artery access has many inadequacies. When a blockage is removed during a procedure, the patient quickly feels better and they often have more energy than they have had in years, but they must remain motionless for several hours. The weight of the sandbag on the femoral artery often causes the lower leg to tingle or go numb. The recovery time from the medical procedure may be as little as ½hour, but the recovery time from the wound can exceed 24 hours. This makes wound site management the longer critical care item. The longer the recovery time, the more expensive the procedure becomes, the greater the patient discomfort, and the greater the risk of complications.

Surgical stapling instruments have been proposed to resolve some of the aforementioned problems associated with vascular procedures. U.S. Pat. No. 5,709,335 issued to Heck discloses a wholly distal surgical stapling instrument for stapling a tubular tissue structure to a luminal structure, such as a vascular lumen. This device can be used for anastomotic stapling of a tubular vessel having two untethered ends, and is especially useful for making the primary anastomotic connection of a bypass vein to a coronary artery or to the aorta. The device essentially includes a rod that is placed within the tubular vessel and anvil that forces staples (associated with the rod) to bend outwardly against the vessel and a target (such as a coronary artery). Thus, this device requires that the stapler device be placed within the tubular vessel (e.g., vein or artery) for operation. While this device is useful when stapling a graft vein or the like, unfortunately, this device would be inappropriate when the entirety of the tubular tissue is not accessible, such as wound closure following an percutaneous transluminal diagnostic procedures and less invasive medical procedures.

Another example is found in U.S. Pat. No. 5,695,504 issued to Gifford, III et al., discloses an end-to-side vascular anastomosis device to perform end-to-side anastomosis between a graft vessel and the wall of a target vessel. This device involves a procedure in which the end of a graft vessel is passed through an inner sleeve of the device until the end of the vessel extends from the distal end of the device. The distal end of the graft is then affixed to the wall of the target, using a staple and stapler which forces a staple into both tissues. Similar to the previous disclosures, this device is useful for the attachment of one tubular tissue onto another, however, is inadequate in sealing a puncture in an artery, vein or other tissue left by certain medical procedures.

Moreover, the prior art has failed to provide a device that permits a doctor or clinician to gain access to a puncture site and remain centered on that site throughout the entire procedure, including closure of the puncture. Additionally, prior art devices do not permit a doctor or clinician to directly or indirectly view the wound site, for example through an endoscope, and thus wound site management is compromised.

SUMMARY OF THE INVENTION

Accordingly, it is an overall object of the present invention to provide a device and method for wound site management during and after medical procedures.

Accordingly, it is an overall object of the present invention to provide a device and method for wound site management and closure during and after medical procedures.

In one aspect, the present invention provides a tissue staple comprising a plurality of prongs connected to a plurality of tabs and arranged about a centerline axis. The prongs have a shoulder portion extending substantially orthogonal from the prong toward the centerline axis. Each prong has a tapered tissue-piercing portion on the distal end thereof.

Alternatively, the staple of the present invention comprises a plurality of prongs arranged about a centerline axis, each prong having a shoulder portion extending substantially orthogonal from the prong toward said centerline axis, and a plurality of web portions connecting each prong to one another, each prong having a tapered tissue-piercing portion on the distal end thereof.

In another aspect, the present invention provides a stapler that includes an elongated sleeve having an inside diameter, an elongated rod with a flared mandrel couple to a distal end, the rod and mandrel sized to fit within the inside diameter of the tube, an actuator mechanism to move the rod relative to the sleeve, a staple adapted to fit between said mandrel and said sleeve, and, said actuator mechanism adapted to move said mandrel relative to said staple and said sleeve causing said staple to close on tissue located about a wound site.

Broader aspects of the stapler include a distal tip comprising a sleeve and a rod inserted into said sleeve, said rod comprising a flared distal tip; an actuator coupled to said sleeve and said rod, said actuator adapted to cause said sleeve to move relative to said rod; and a tissue staple comprising a plurality of tissue piercing prongs placed around said rod between said sleeve and said flared distal tip.

Wound closure procedures according to the present invention include a process for closing a wound comprising the steps of: inserting an introducer into a tissue wound, placing a sheath around the introducer and locating the sheath approximate to said wound, inserting the distal end of a stapler into said sheath to approach the tissue wound site, said stapler including a tissue staple on the distal end of said stapler, expanding a portion of the staple about said wound, and contracting at least a portion of said staple pulling the tissue surrounding the wound together.

Other wound closing methods include a process for closing a wound in an artery with a staple, comprising the steps of: inserting an introducer with a plurality of guide wires coupled thereto into an artery, guiding a stapler and staple to the wound site, expanding said staple to surround said wound site before entering said tissue, and closing said staple on said tissue to close said wound.

In yet another aspect, the present invention provides an introducer that includes a sheath having an inside diameter and a distal end, a dilator sized to fit within the inside diameter of the sheath, and a plurality of flexible wire guides having first ends and second ends, the first ends coupled to the distal end of the sheath, wherein the sheath being approximated to a wound site and the wire guides placed approximate to tissue surrounding the wound site to hold said sheath approximately centered on said wound site.

In broader embodiment, the introducer of the present invention includes a tubular sheath, and at least one flexible wire guide affixed to the sheath, said wire guide placed approximate to tissue surrounding a wound site to hold said sheath approximately centered on said wound site.

In method form, the present invention also includes wound site stabilization methodology including the steps of: approximating an elongated sheath to a wound site;

inserting one or more wire guides into the wound site; placing said wire guides approximate to tissue surrounding said wound site; and allowing opposing sides of said tissue surrounding said wound site to approximate one another. Other procedural embodiments include a method for stabilizing a wound site, comprising the steps of: approximating an elongated sheath to a wound site; inserting one or more wire guides into the wound site; placing said wire guides approximate to tissue surrounding said wound site; and centering said sheath about said wound site.

It will be appreciated by those skilled in the art that although the following Detailed Description will proceed with reference being made to preferred embodiments, the present invention is not intended to be limited to these preferred embodiments. Other features and advantages of the present invention will become apparent as the following Detailed Description proceeds, and upon reference to the Drawings, wherein like numerals depict like parts, and wherein:

BRIEF DESCRIPTION OF THE DRAWINGS

FIG. 7 depicts one embodiment of the stapler of the present invention;

FIG. 8 is an isometric view of the distal tip of the stapler of FIG. 7 adapted to hold and deploy the staple of FIGS. 1–6;

FIG. 22A depicts a detailed view of the sheath of the present invention;

FIG. 24A depicts a detailed view of the sheath of the present invention;

FIG. 25A depicts a detailed view of the sheath of the present invention; and FIGS. 18–26 depict various views of procedural embodiments of the present invention, including FIG. 20 depicting one embodiment of the introducer of the present invention.

DETAILED DESCRIPTION OF THE INVENTION

Tissue Staple

In one aspect of the present invention, a staple is provided to close a tissue wound after a medical procedure. Although the preferred use of the staple of the present invention is to close an artery or vein following a diagnostic or interventional procedure, it should be recognized at the outset that the staple may be used for general tissue repair, not just limited to vascular repair. It will be appreciated throughout the following description that the staple of the present invention can be formed of any biocompatible and/or bioabsorbable materials, including, for example, Titanium (and Titanium alloys), stainless steel, polymeric materials (synthetic and/or natural), ceramic, etc. It will also be apparent from the following description that the staple of the present invention is preferably formed of a deformable material (such as those listed above) that undergoes plastic deformation (i.e., deformation with negligible elastic component.) As a general overview, the staple of the present invention undergoes two positions of deformation: a first position to extend the distal ends of the prongs of the staple outwardly to grab a greater amount of tissue (and also to grab tissue away from the wound locus), and a second position to move the prongs inwardly to close the wound.

Figure 1:
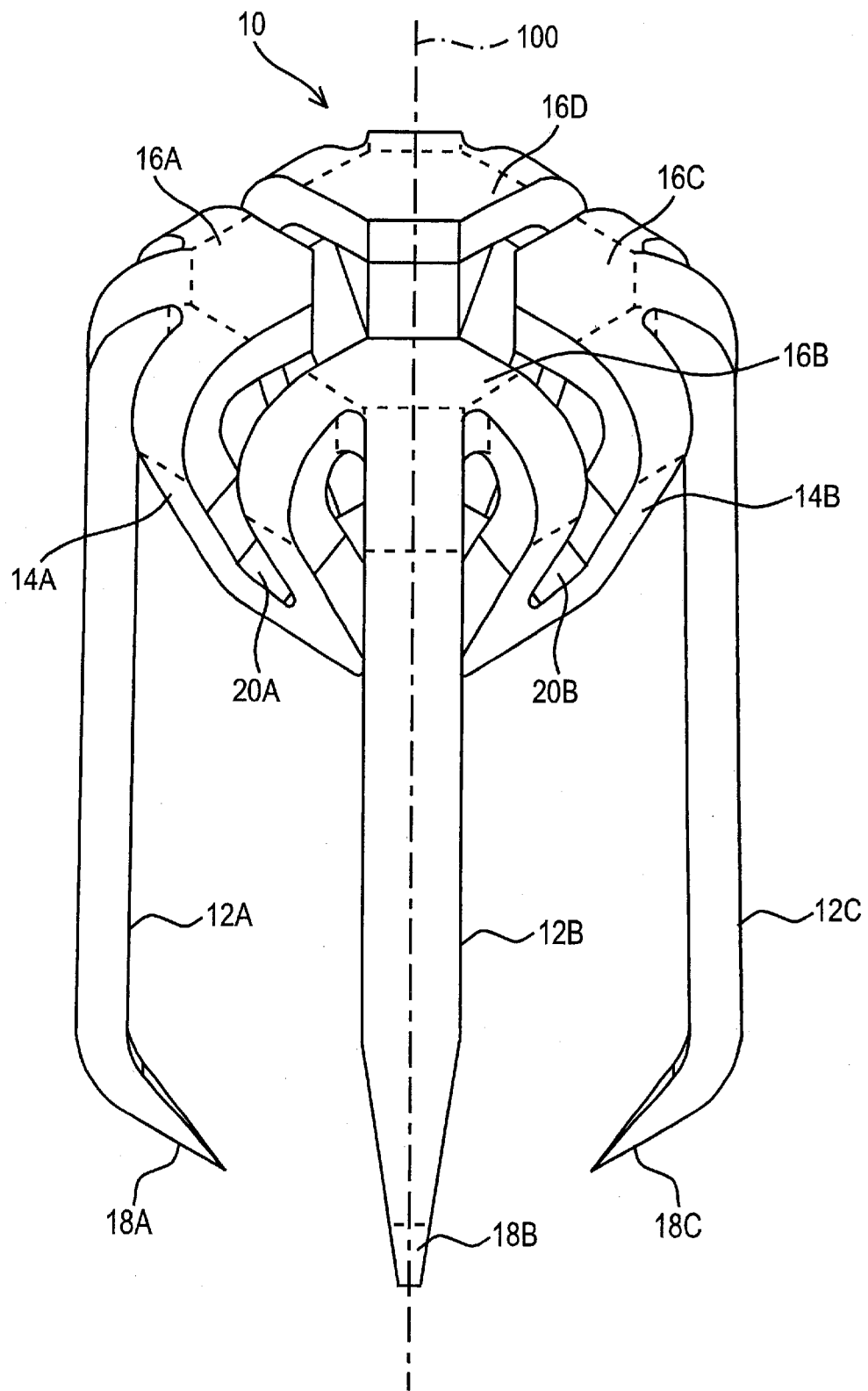
FIGS. 1–3 are isometric views of one embodiment of the staple of the present invention in formed, opened and deployed positions, respectively.
Figure 2:
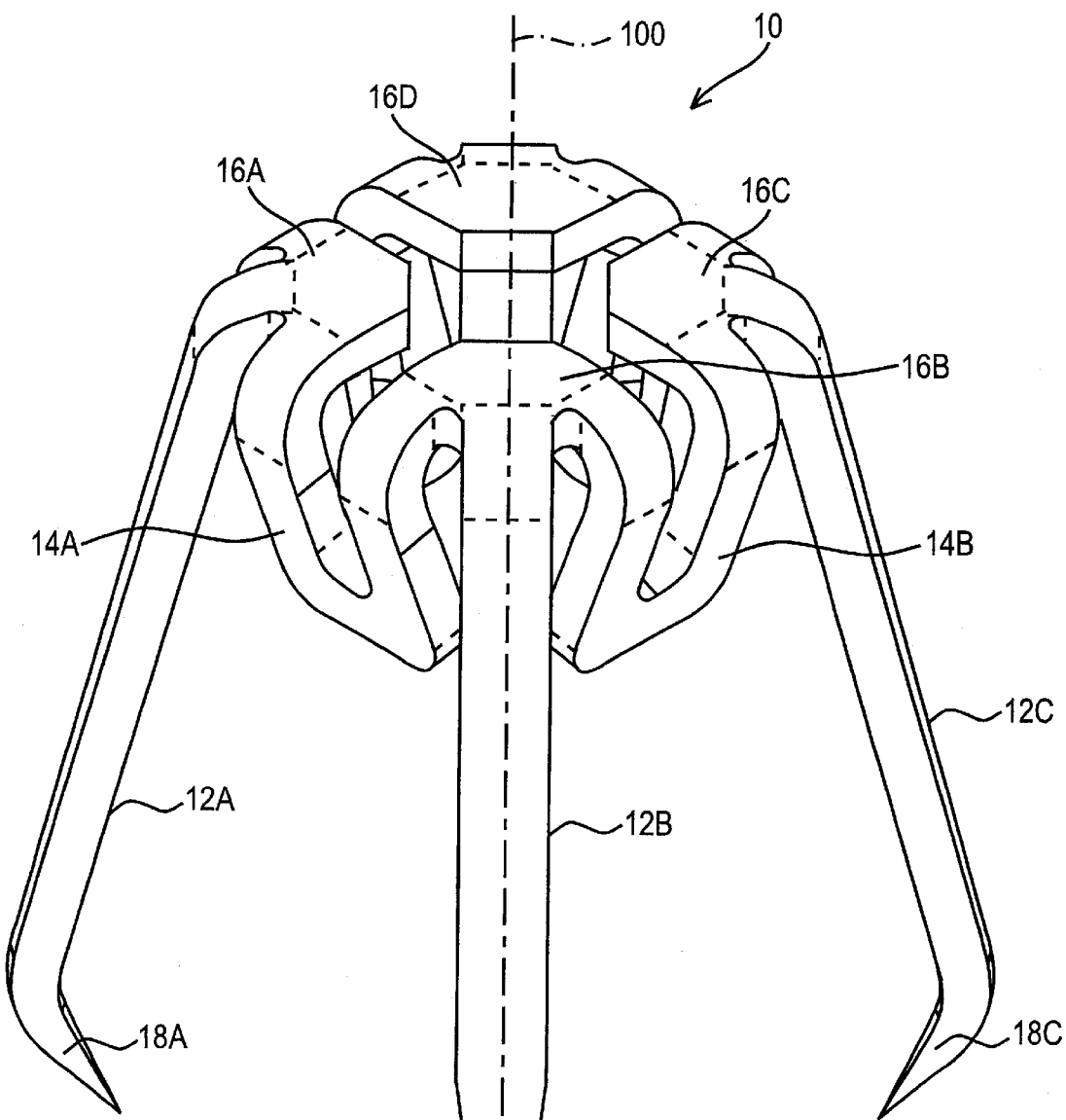
Figure 3:
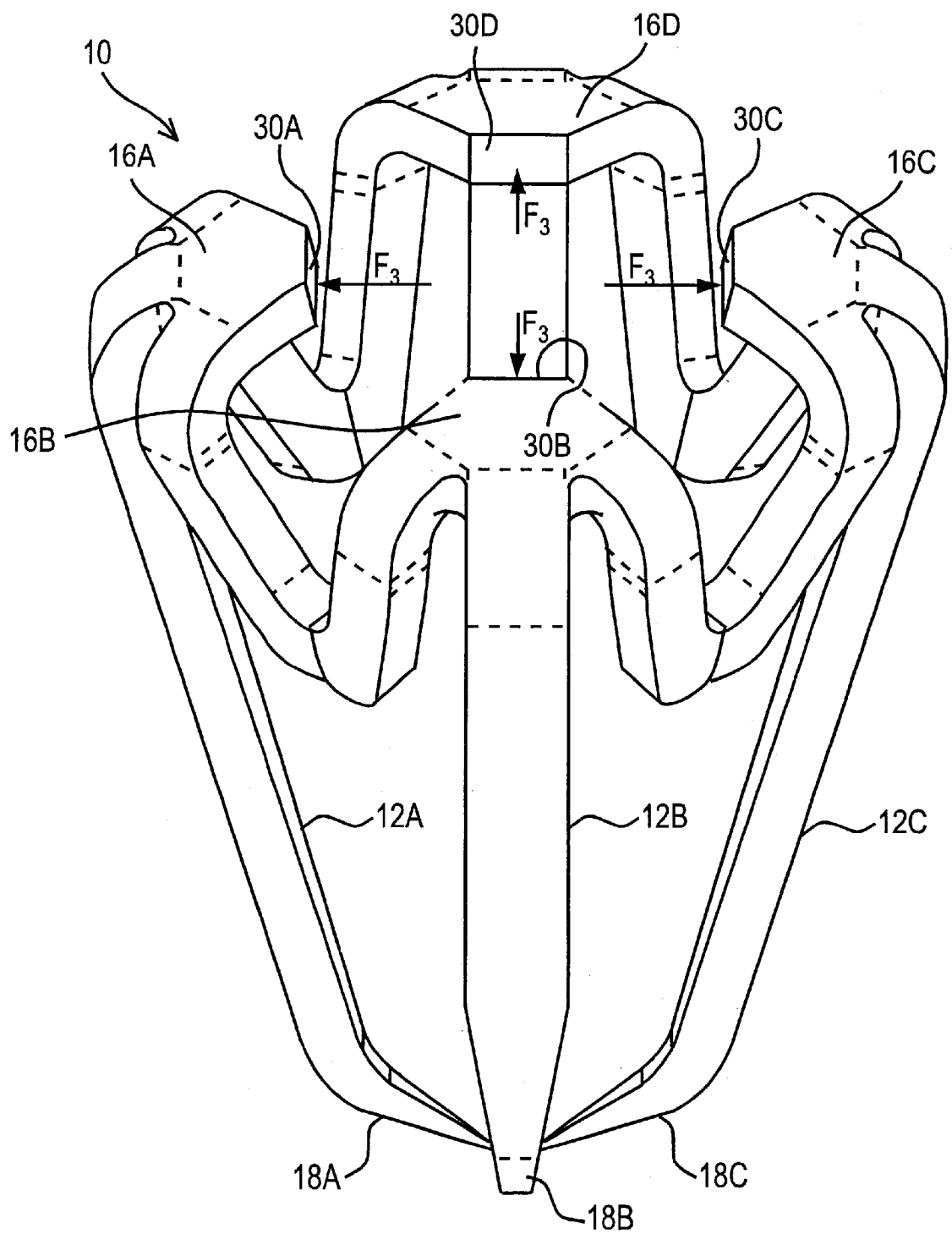

FIGS. 1, 2 and 3 depict one embodiment of staple 10 of the present invention. FIG. 1 is the staple in it's formed position, FIG. 2 is the staple just prior to deployment into tissue with the prongs extended outwardly, and FIG. 3 is the staple closed around tissue. The staple 10 of this embodiment comprises a plurality of prongs 12A–12D and a plurality of tabs 14A–14D, arranged about a centerline axis 100. Common portions, or shoulders 16A–16D are formed where the tabs meet the prongs. Each shoulder is common to both the prong and the tab and is generally defined by a relatively flat portion generally orthogonal to the centerline axis. Shoulders 16A–16D may be viewed as an extension of each prong, bent inwardly toward the centerline axis. Each of these features of the staple 10 of this embodiment is detailed below.

In the formed position (FIG. 1), prongs 12A–12D extend generally parallel to central axis 100, as shown. At the distal end of each prong, tapered points 18A–18D is formed to extend inwardly toward the centerline axis 100. At the proximal end, shoulders 16A–16D meet at prongs 12A–12D, respectively. Tabs 14A–14D are generally U-shaped, and are formed between each prong. The proximal portions of each tab are joined at consecutive shoulders, as shown. Each proximal portion of the U (i.e., each "leg" of the U-shape tab) extends first generally outward from the shoulder, and second bends inwardly and distally toward centerline axis 100, connecting together nearest the centerline axis to form the U shape. The U-shape defines slots 20A–20D within each tab having a base positioned at the bottom thereof.

Figure 2A:
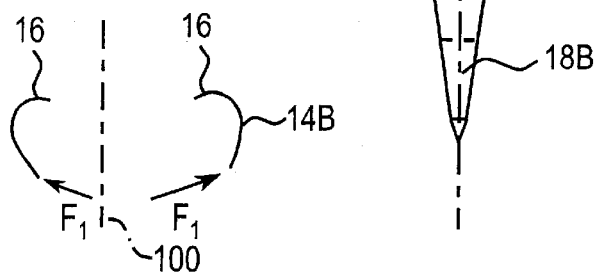
FIG. 2A depicts a deformed staple of the present invention.

Referring specifically to FIG. 2, the staple 10 is deformed so that prongs 12A–12D extend outwardly from the centerline axis, prior to deployment into tissue. It is advantageous to extend the prongs outwardly as shown so as to grasp a large portion of tissue, and so that insertion of the prongs into the tissue occurs at a locus away from the wound site, thereby providing a more consistent wound closure (by closing the wound with more of the surrounding tissue) and ensuring complete (or near complete) closure of the wound. To deform the staple into the position shown in FIG. 2, a force $F_1$ is applied to tabs 14A–14D, as shown in relief in FIG. 2A. Force $F_1$ is generally outward (from the centerline axis) and proximal to the top of the staple, as shown in relief in FIG. 2A. This force causes the tabs to move outward from the centerline axis 100. The outward movement of the tabs causes the shoulder portions to pivot roughly about the juncture between the shoulder and the prong (i.e., at the outer portion of the shoulder), causing the inner portions of the shoulders to move inwardly toward the centerline axis and distally. Since the prongs are attached to the outer portion of the shoulders, the movement of the shoulders in this manner causes the prongs to move outwardly. Thus, the cross-sectional diameter of the staple gets larger at the distal end (with respect to the cross-sectional diameter of the formed staple of FIG. 1). Note that the movement of the prongs is generally greater at the distal portions thereof than at the proximal portions thereof. In other words, movement of the prongs as shown in FIG. 2 is pivoted from the shoulder, thus producing a staple with outwardly extending prongs. For completeness, it should be noted that a holding force may be applied downwardly (i.e., substantially parallel to the centerline axis) against the base of the slots 20A–20D to hold the staple in place. Also, it is preferred that these forces are simultaneously applied to each tab of the staple to produce uniform deformation of each prong of the staple. As mentioned above, it is preferable that the plastic deformation of the staple is semi-permanent, so that the staple does not tend to return to the shape depicted in FIG. 1 (i.e.,non-elastic deformation). Deformation of the staple into this position will be described in greater detail below in reference to the preferred stapler device of the present invention.

FIG. 3 depicts the staple 10 in a closed position. The closed position, as stated herein generally means that the prongs of the staple are moved inwardly toward each other. Although FIG. 3 depicts the tapered tip portions of the prongs meeting generally in the vicinity of the centerline axis, however, it should be understood that the term "closed" or "deployed" as used in reference to the staple need not necessarily mean this precise configuration. It may be required (or desirable) for some procedures to move the prongs inwardly toward each other to a greater or lesser extent than as depicted in FIG. 3. To draw the staple into the closed position depicted in this Figure, a force $F_3$ is applied to the inner surfaces 30A–30D of the shoulds. This force is generally orthogonal to the centerline axis, and the angle between each force approximates the angle between the inner surfaces 30A–30D (which, in the staple of this embodiment is approximately 90 degrees). This force causes the slots 20A–20D to spread apart and urges the shoulders outwardly. Movement in this manner also causes the shoulders to move outwardly and proximally. Proximal movement of the shoulders causes the prongs to move toward each other. Opposite to the movement of FIG. 2, deformation shown in FIG. 3 results in an expanded cross-sectional diameter of the proximal end of staple, and a diminished cross-sectional diameter of the distal end of the staple (with respect to the formed staple of FIG. 1 and the deformed staple of FIG. 2). Again, deformation of the staple 10 into this position will be described in greater detail below in reference to the preferred stapler device of the present invention.

For certain tissue applications, it may be desirable that the staple of the present invention is deployed into tissue such that the prongs do not fully pierce through the tissue, but rather grasp and hold the tissue together. For example, for vascular closure applications it may be desirable that the tissue piercing tapered ends not enter the bloodstream, but rather pierce into the tissue and stop short of piercing through the tissue wall. To that end, and referring to FIG. 3A, the staple 10' of the present invention can be adapted with tissue stops 32A–32D. Preferably, tissue stops 32A–32D are located along the length of each prong, and positioned from the distal tip of the prong to permit the tapered ends to pierce tissue, but not pierce all the way through the tissue. Accordingly, the position of the stops 32A–32D along the length of the prongs is selected to facilitate tissue grabbing (but not complete tissue piercing) and can vary from application to application.

Figure 4:
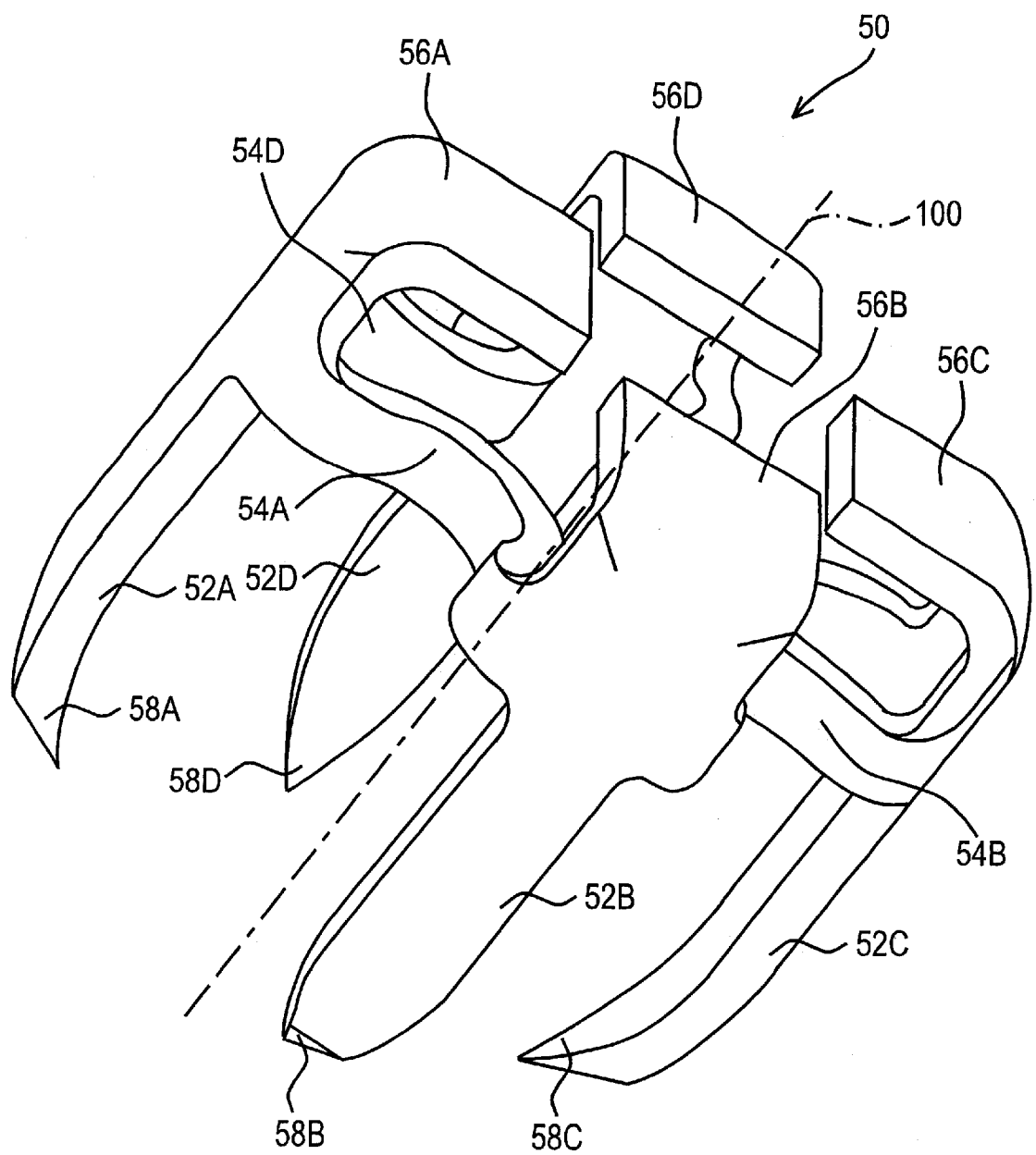
FIGS. 4–6 are isometric views of another embodiment of the staple of the present invention in formed, opened and deployed positions, respectively.
Figure 5:
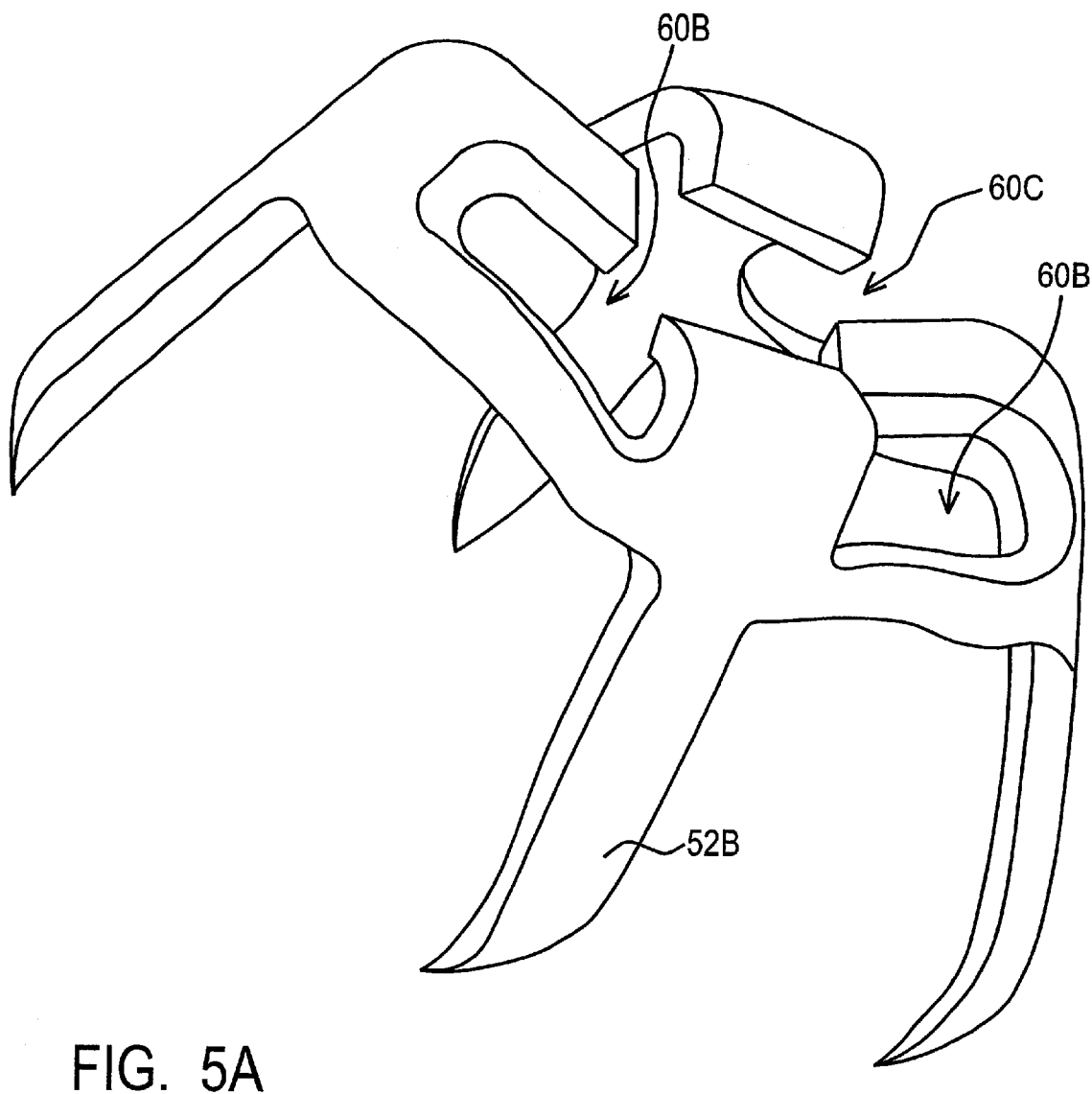
Figure 6:
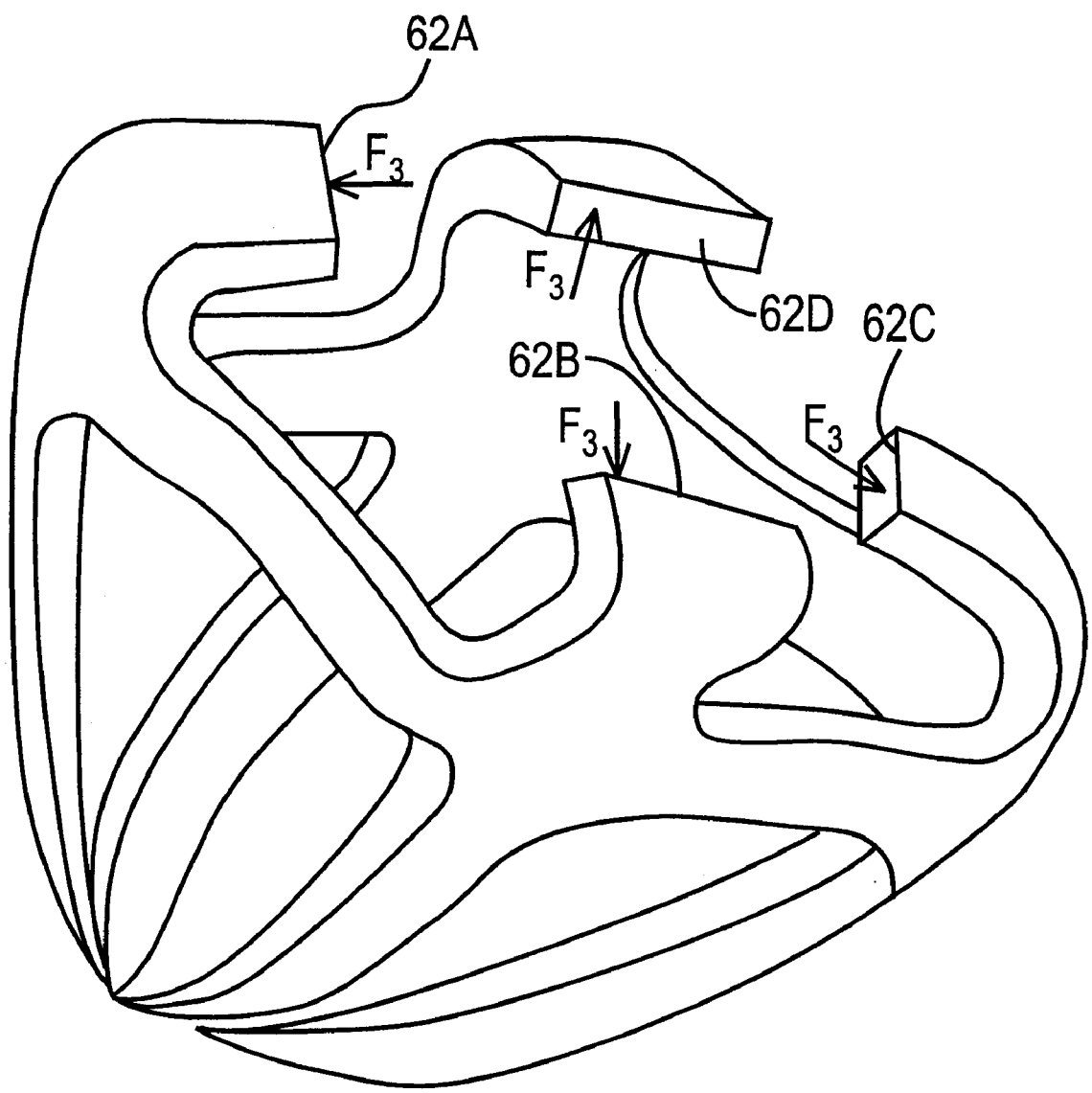

FIGS. 4–6 depict another embodiment of a staple 50 of the present invention. FIG. 4 is the staple in it's formed position, FIG. 5 is the staple just prior to deployment into tissue with the prongs extended outwardly, and FIG. 6 is the staple closed around tissue. Similar to the first embodiment, the staple 50 of this embodiment comprises a plurality of prongs 52A–52D arranged about a centerline axis 100. A shoulder 56A–56D is provided and is generally defined by a relatively flat surface, generally orthogonal to centerline axis. Shoulders 56A–56D may be viewed as an extension of each prong, bent inwardly toward the centerline axis. In this embodiment, webs 54A–54D are connected to and between each prong, and are formed to extend inwardly from each prong toward the centerline axis, creating a U shape generally orthogonal to the centerline axis (as opposed to the previous embodiment in which the U-shaped tab is positioned generally parallel to the centerline axis). Each of the features of the staple 50 of this embodiment is detailed below.

In the formed position (FIG. 4), prongs 52A–52D extend generally parallel to central axis 100, as shown. At the distal end of each prong, tapered points 58A–58D are formed to extend inwardly toward the centerline axis 100. At the proximal end, shoulders 56A–56D meet at prongs 52A–52D, respectively. Web portions (webs) 54A–54D are generally U-shaped, and are formed between each prong extending inwardly toward the centerline axis. As shown, webs connect the prongs at a position distal to the shoulders. The precise position of the webs is determined by the desired extent to which the prongs are extended outwardly, and the extent to which the web curves inward toward the centerline axis. The space between the shoulders and the web portions defines a slot 60A–60D.

Figure 5A:
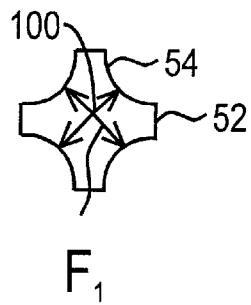

Referring specifically to FIG. 5, the staple 50 is deformed so that prongs 52A–52D extend outwardly from the centerline axis, prior to deployment into tissue. As with the previous embodiment, it is advantageous to extend the prongs outwardly as shown so as to grasp a large portion of tissue, and so that insertion of the prongs into the tissue occurs at a locus away from the wound site, thereby providing a more consistent wound closure (by closing the wound with more of the surrounding tissue) and ensuring complete (or near complete) closure of the wound. To deform the staple into the position shown in FIG. 5, a force $F_1$ is applied to webs 54A–54D, as shown in relief in FIG. 5A. Force $F_1$ is generally outward from the centerline axis and causes the webs to deform outwardly, i.e. straightening the bend of the web by moving the centermost point of the web outwardly. By deformation of the web portions in this manner, the prongs, move outwardly. Thus, the cross-sectional diameter of the staple gets larger at the distal end (with respect to the cross-sectional diameter of the formed staple of FIG. 4). Note that the movement of the prongs is generally greater at the distal portions thereof than at the proximal portions thereof, thus producing a staple with outwardly extending prongs. For completeness, it should be noted that a holding force may be applied downwardly (i.e., substantially parallel to the centerline axis) against the top of the webs in slots 60A–60D to hold the staple in place. Also, it is preferred that these forces are simultaneously applied to each web of the staple to produce uniform deformation of each prong of the staple. As mentioned above, it is preferable that the deformation of the staple is plastic, so that the staple does not tend to return to the shape depicted in FIG. 4. Deformation of the staple into this position will be described in greater detail below in reference to the preferred stapler device of the present invention.

FIG. 6 depicts the staple 50 in a closed or deployed position. The closed position, as stated herein generally means that the prongs of the staple are moved inwardly toward each other. To draw the staple into the closed position depicted in this Figure, a force $F_3$ is applied to the inner surfaces 62A-62D of the shoulders. This force is generally orthogonal to the centerline axis, and the angle between each force approximates the angle between the inner surfaces 62A–62D about the centerline axis (which, in the staple of this embodiment is approximately 90 degrees). This force urges the shoulders outwardly. Note that shoulders can only extend outwardly as far as the web portions will permit. Outward movement of the shoulders causes the prongs to move toward each other, since, there is a general pivot about the web portions. Opposite to the movement of FIG. 5, deformation shown in FIG. 6 results in an expanded cross-sectional diameter of the proximal end of staple, and a diminished cross-sectional diameter of the distal end of the staple (with respect to the formed staple of FIG. 4 and the deformed staple of FIG. 5). Again, deformation of the staple 50 into this position will be described in greater detail below in reference to the preferred stapler device of the present invention.

In either embodiment described above, it should be evident that although the Figures depict four each of the prongs, tabs and shoulders, this should be only be considered exemplary. It may be desirable to adapt the staple 10 or the staple 50 with more or fewer prongs, tabs and shoulders for a given application. Also, it is not necessary that each prong is the same length, or that each prong has the same overall dimensions. In alternative embodiments, the entire staple, or selected portions thereof can be alternatively fashioned from an elastic or shape memory (e.g., nitinol,.and/or other elastic materials, including for example temperature dependant shape memory materials) material thereby permitting elastic deformation from the a static closed position to an expanded position and then elastically close about the wound. Also, the embodiment of FIGS. 4–6 can be adapted with a tissue stop positioned along the length of the prong, as shown in FIG. 3A.

Figure 3A:
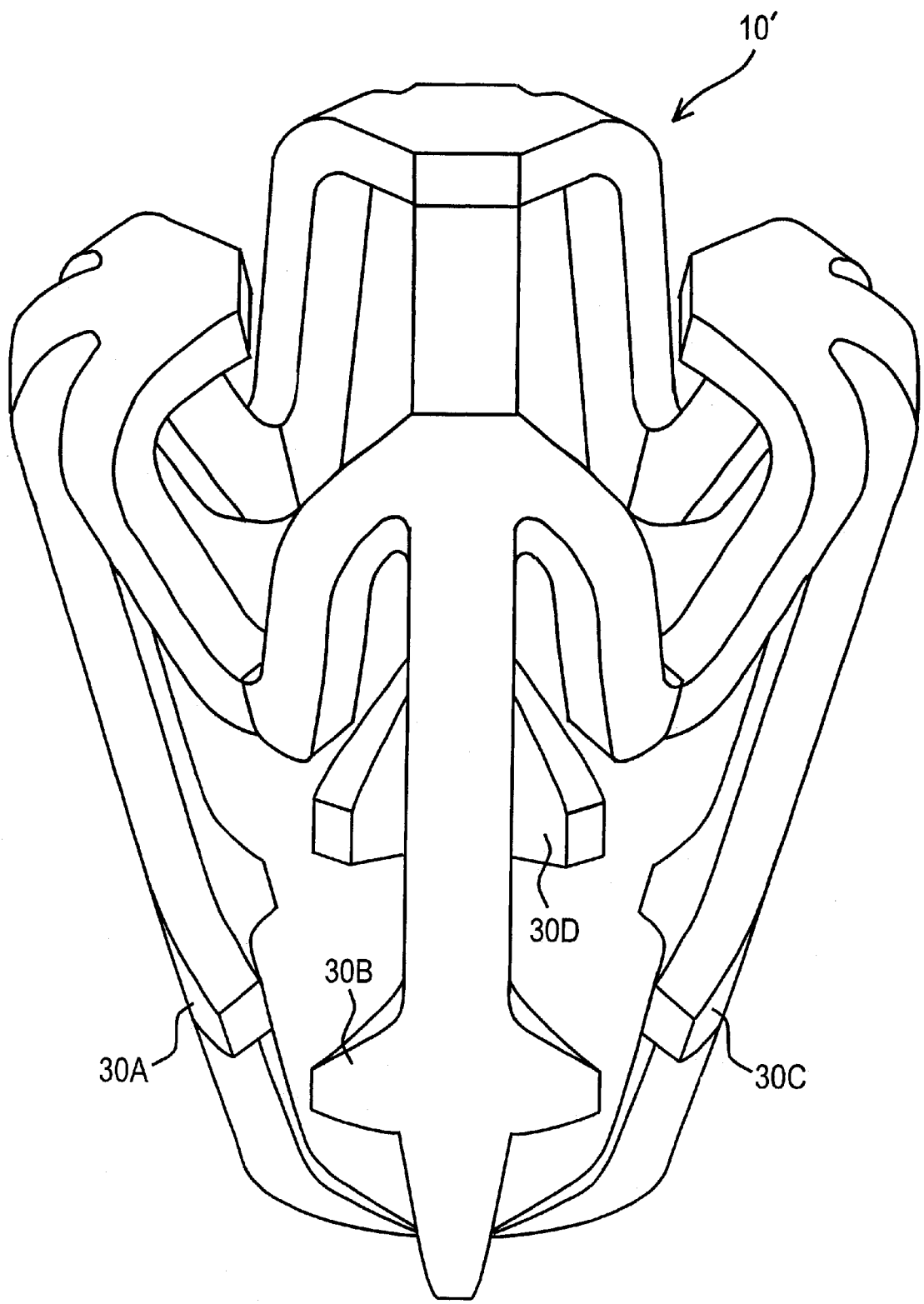
FIG. 3A depicts an isometric view of alternative staple of the embodiment of FIGS. 1–3.

Stapler Device p Another aspect of the present invention is a stapler device to deploy the staple 10 of FIGS. 1–3, the staple 10' of FIG. 3A, and the staple 50 of FIGS. 4–6. As a general overview, the stapler of the present invention includes a distal tip for holding and deploying a staple, and an actuator mechanism to cause a staple, or at least the tissue piercing portions of a staple, to expand outwardly and then close about a wound. The stapler of the present invention facilitates one object of the present invention to ensure that the staple closes a greater amount of tissue as compared with conventional stapling mechanisms. The following description will detail various exemplary mechanisms to accomplish this goal, but it should be recognized that numerous alternatives will be readily apparent to those skilled in the art, and all such alternatives are to accomplish these objectives are deemed within the scope of the present invention.

FIG. 7 depicts an isometric view of one embodiment of a stapling device 100 of the present invention. The device generally includes an actuation mechanism 104 and a distal tip 102. FIG. 8 is a more detailed view of the distal tip 102 of the stapler device 200. The distal tip preferably comprises an inner rod member 110 slidable within an outer sleeve 112. Rod 110 includes a flared or mandrel portion 114. Mandrel 114 also includes slots 118A–118D, which in use are aligned with fingers 116A–116D. Fingers 116A–116D mate with slots 20A–20D and 60A–60D of the staple 10 and 50, respectively. Preferably, rod 110 is removable for staple attachment thereto, where a staple is positioned between the mandrel and the sleeve. The mandrel, as will be described below, is responsible for the forces generated on the staple.

Figure 9B:
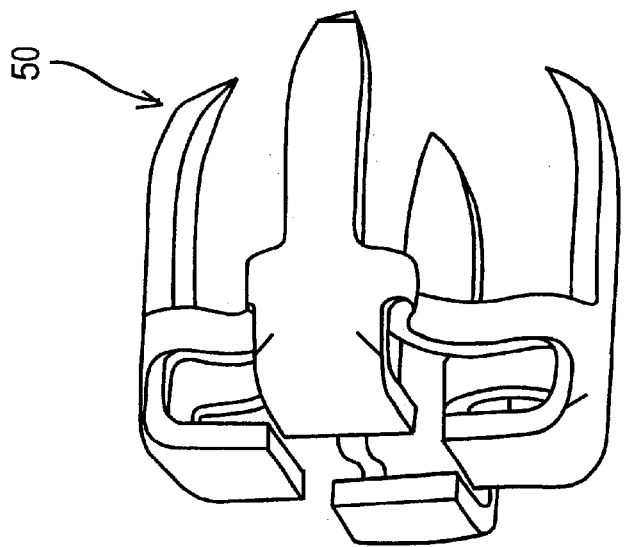
FIGS. 9A–11B are isometric views of the cooperative movement of the distal tip of the stapler and the staple of the present invention.
Figure 9A:
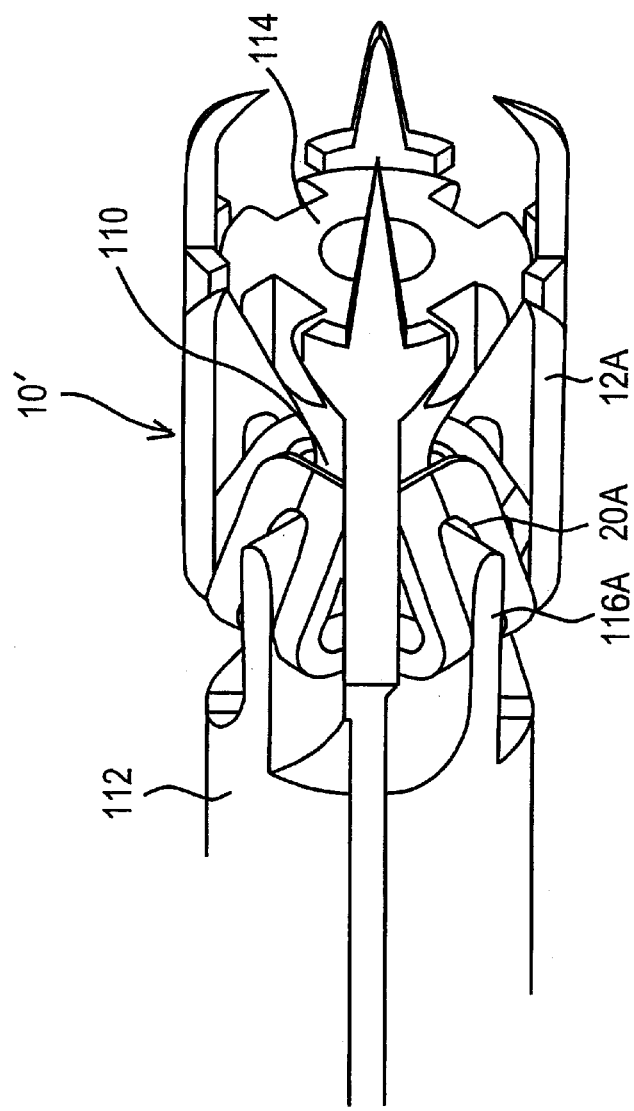
Figure 10A:
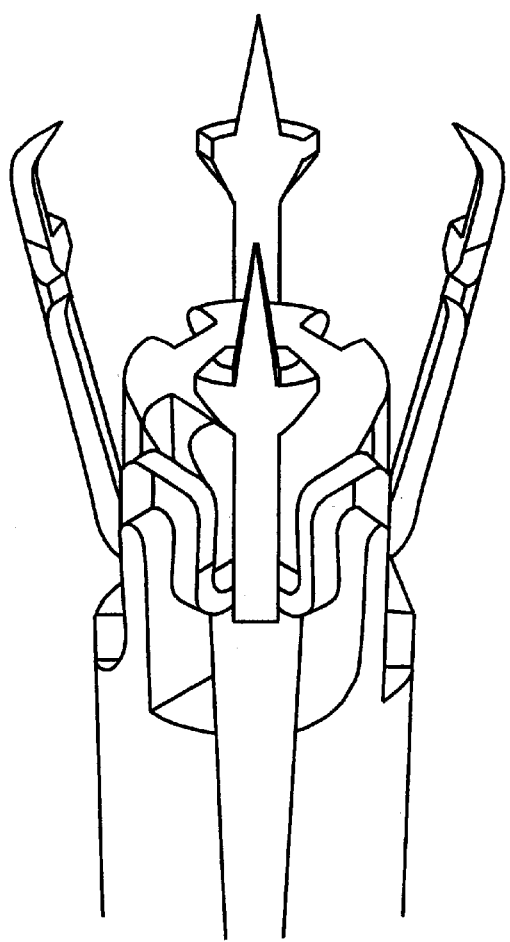
Figure 10B:
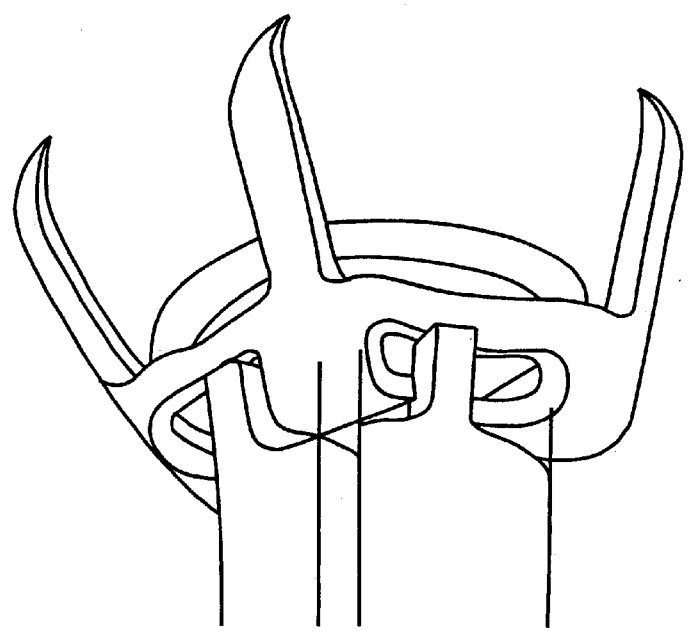
Figure 11B:
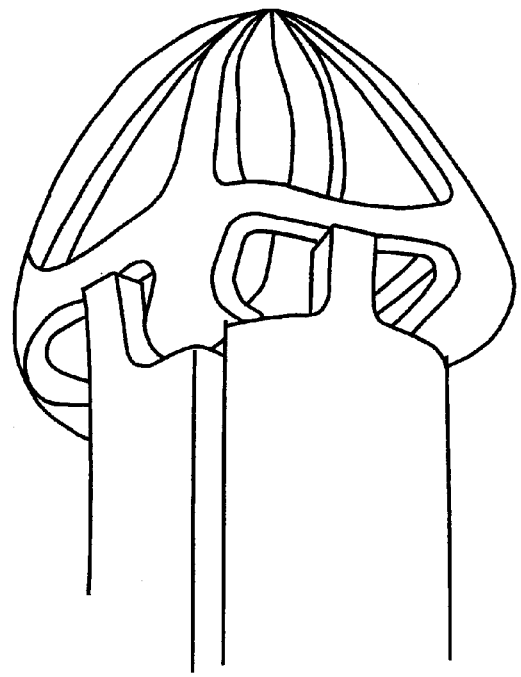
Figure 11A:
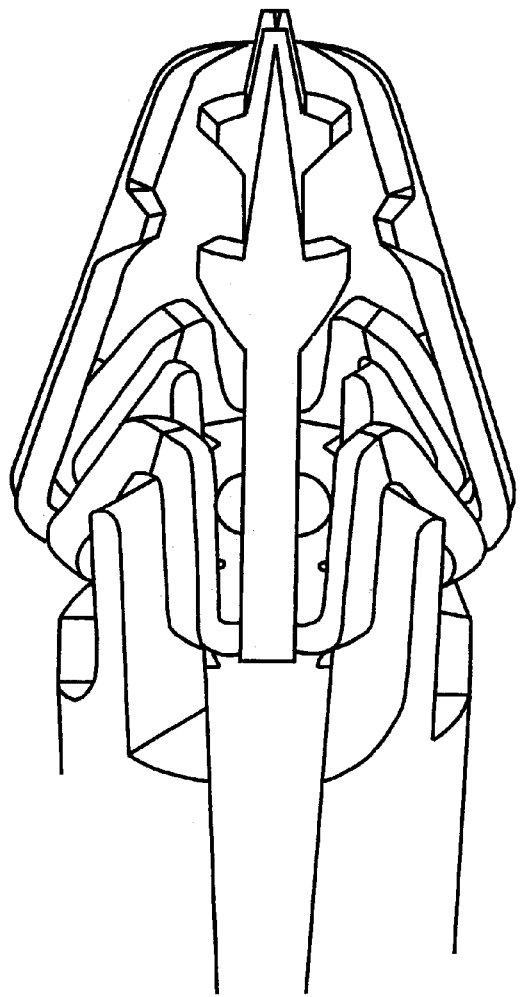

FIGS. 9, 10A, 10B, 11A and 11B depict the working relationship between the staple 10' and/or 50 of the present invention and the mandrel 114/sleeve 112 of the stapler mechanism 200. In FIG. 9A, the staple 10' is placed between the mandrel 114 and sleeve 112. Slots 20A–20D of the staple engage fingers 116A–116D of the sleeve. The prongs 12A–12D of the staple are dimensioned so as to fit over the mandrel, and tabs 14A–14D are dimensioned so as to fit over the rod 110, as shown. Similarly, for the staple 50 shown in FIG. 9B the staple 50 engages the mandrel 114 and sleeve 112 (not shown). This is a static position, as no forces are applied to the staple to cause deformation. In FIG. 10B, the staple 10'is urged into the first deformed position (of FIG. 2), by the relative movement of the rod/mandrel and the sleeve. As shown, the mandrel is urged proximally. As the mandrel moves, the tabs of the staple meet the narrowest part of the mandrel. Further movement forces the tabs to move outwardly, causing the prongs to likewise move outwardly (as described above with reference to FIG. 2). Once the tabs clear the mandrel, outward, movement of the tabs and prongs ceases. Similarly, in FIG. 10B, the movement of the mandrel forces webs to extend outwardly causing the prongs to extend outwardly (as described above with reference to FIG. 5). Once the webs clear the mandrel, outward movement of the prongs ceases. FIG. 11A depicts final deployment of the staple into tissue. As the mandrel is drawn further proximally and once the tabs have cleared the mandrel, the shoulders (not shown) are spread outward, forcing the prongs to move together (toward the centerline axis) and closing tissue therebetween. Figure 11B depicts the same actuation, but for the staple 50 of FIGS. 4–6.

Figure 12:
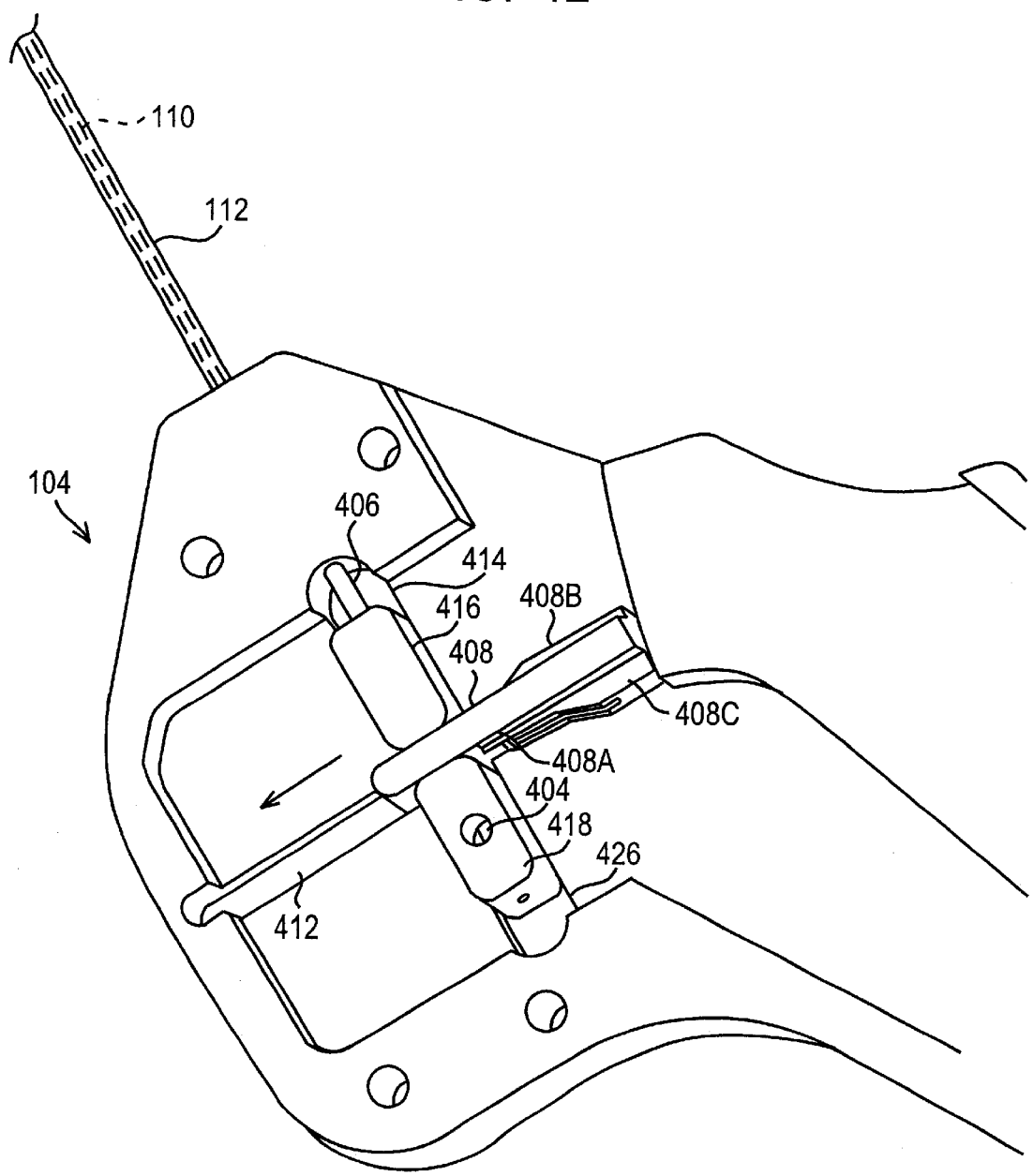
FIGS. 12–15 are isometric views of an exemplary staple deployment mechanism of the stapler of the present invention.

FIGS. 12–15 depict an exemplary actuator mechanism 104, showing the relative motion of the sleeve 112 and the mandrel rod 110. The mechanism includes a cam 408 movable in a linear motion along a slot 412. Movement of the cam can be manual or through an electronically controllable motor (not shown). The cam 408 has lobes 408A and 408C located on a first side of the cam 408 and a lobe 408B located on a second and opposing side of the cam 408. A first cam follower 418 is coupled to the mandrel rod 110, and is selectably engagable with lobes 408A and 408C. A second cam follower 416 is coupled to the sleeve 112, and is selectably engagable with lobe 408B. FIG. 12 depicts that neither cam follower is in contact with the lobes, and is indicative of an initial position of the mechanism.

Figure 13:
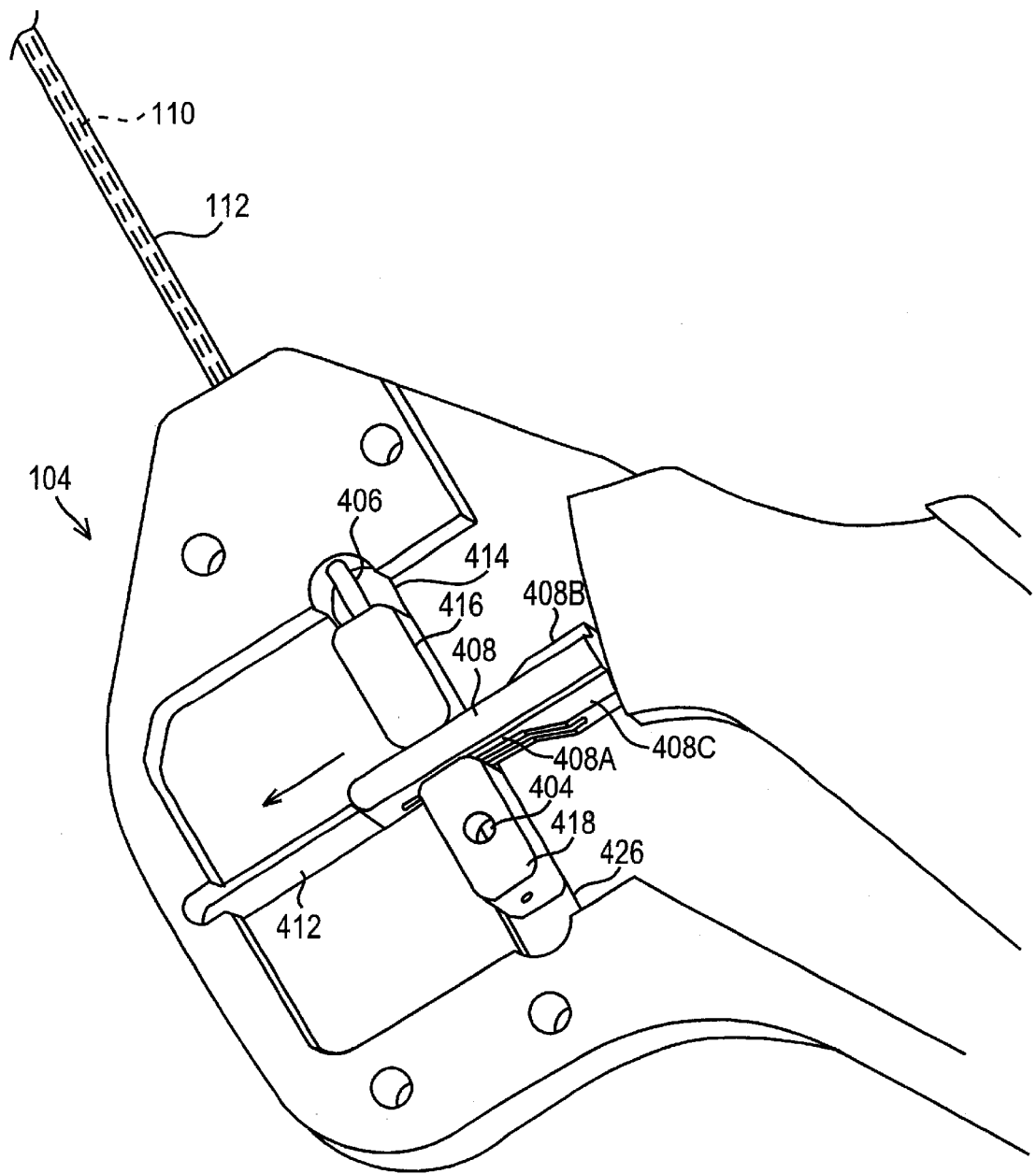
Figure 14:
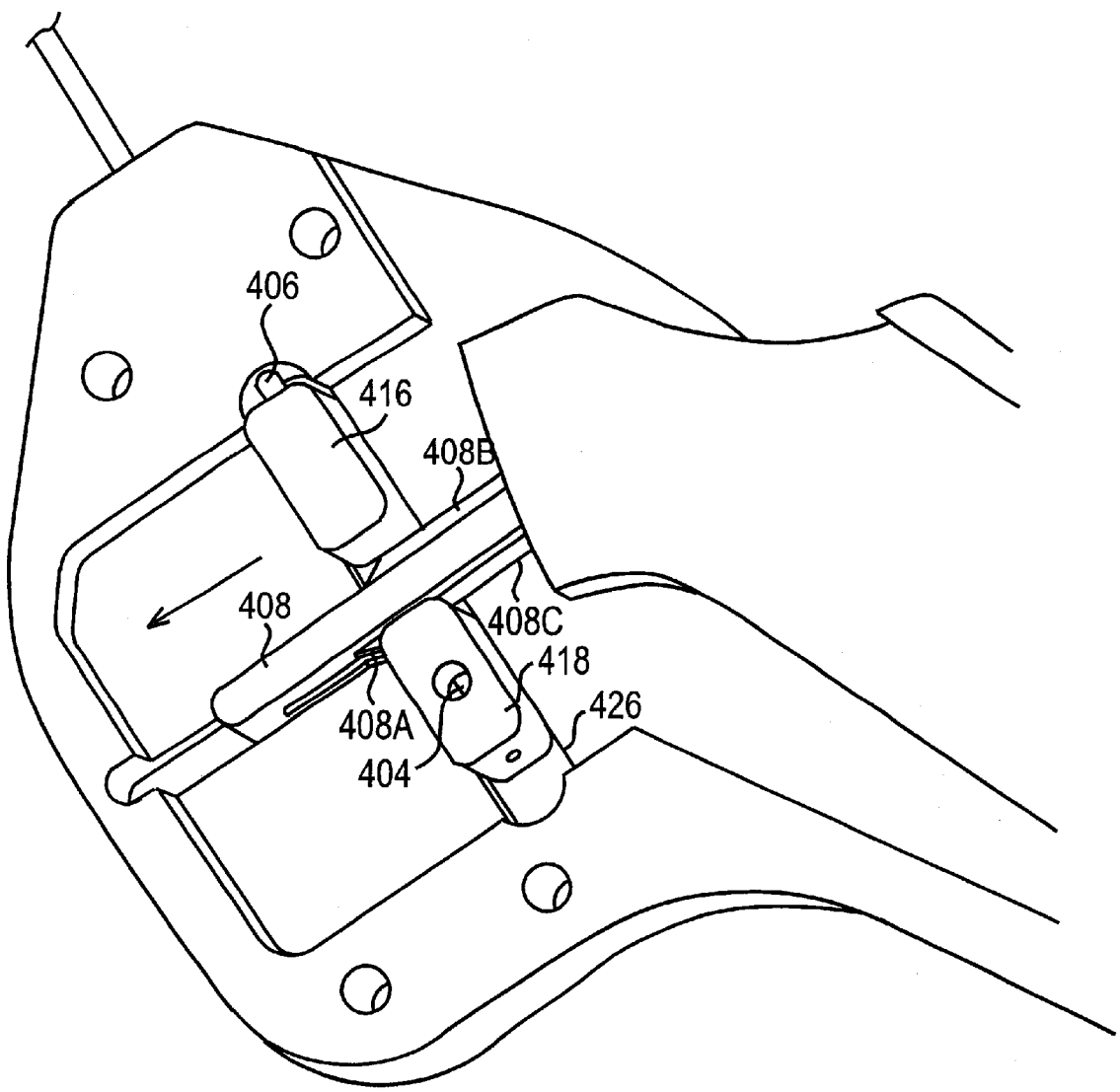
Figure 15:
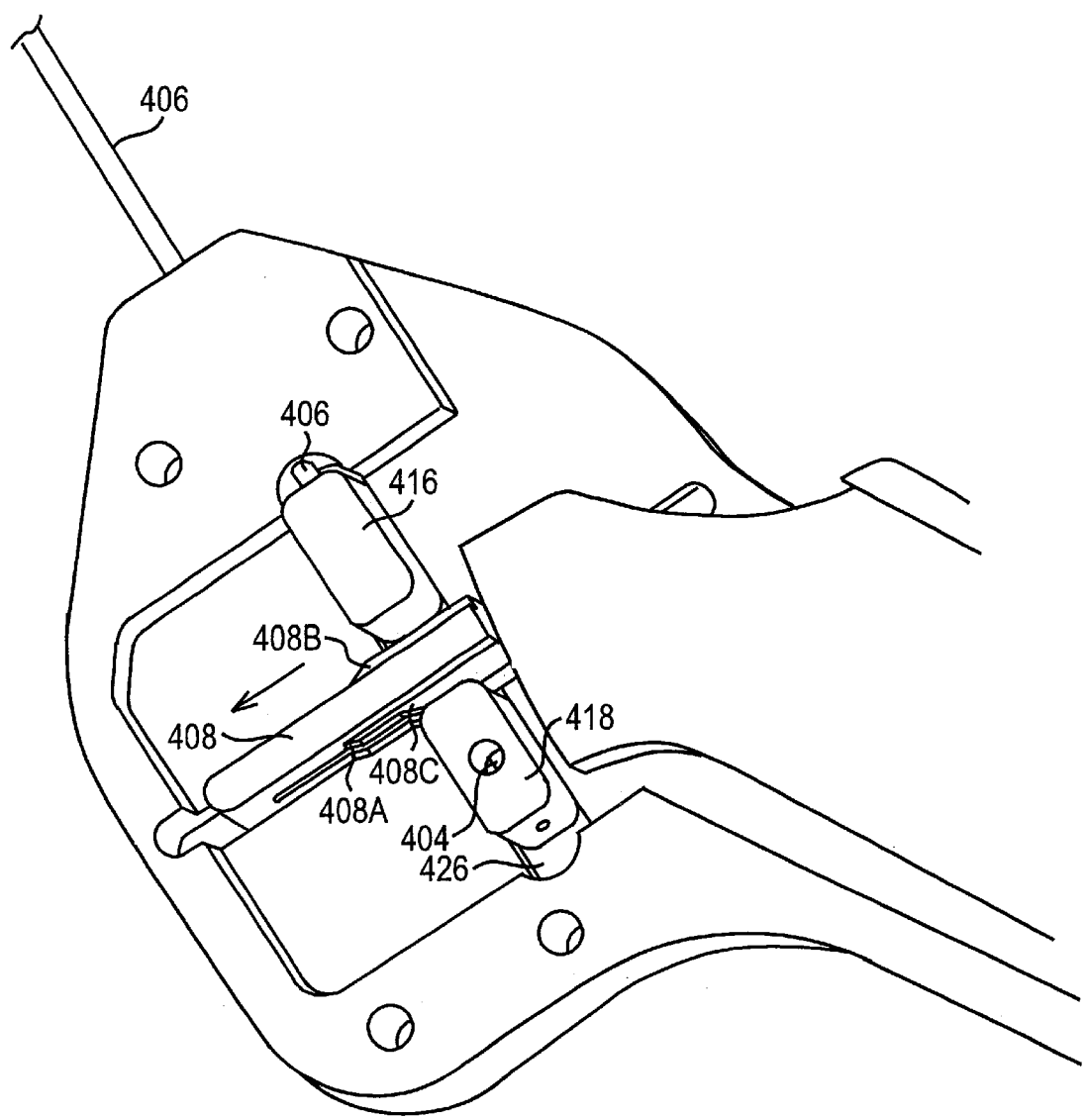

FIG. 13 depicts the mechanism 104 in a position to expand the staple between the mandrel 114 and the sleeve 112, as shown in FIG. 9A. As cam 408 is moved (as indicated by the arrow), lobe 408A urges cam follower 418 along slot 426. The mandrel rod 110 is moved proximally, causing the prongs to extend outwardly (as shown in FIGS. 2 and 5) as a result of the force of the mandrel 114 on the tabs or the web portions. With further movement of the cam 408 (FIG. 14), lobe 408B now urges cam follower 416 to move distally, thereby moving the sleeve distally relative to the mandrel rod and causing further expansion of the prongs and causing the staple to move distally. Finally, in FIG. 15, the cam is urged yet further and cam follower 418 is urged by lobe 408C causing the mandrel and madrel rod to extend further proximally. This relative movement between the cam rod and the sleeve causes the mandrel to apply a force to the shoulder portions of the staple, in turn causing inward movement of the prongs. Lobe 408C causes closure of the prongs and decouples the staple from the mandrel. This is the fully deployed staple movement.

Figure 16:
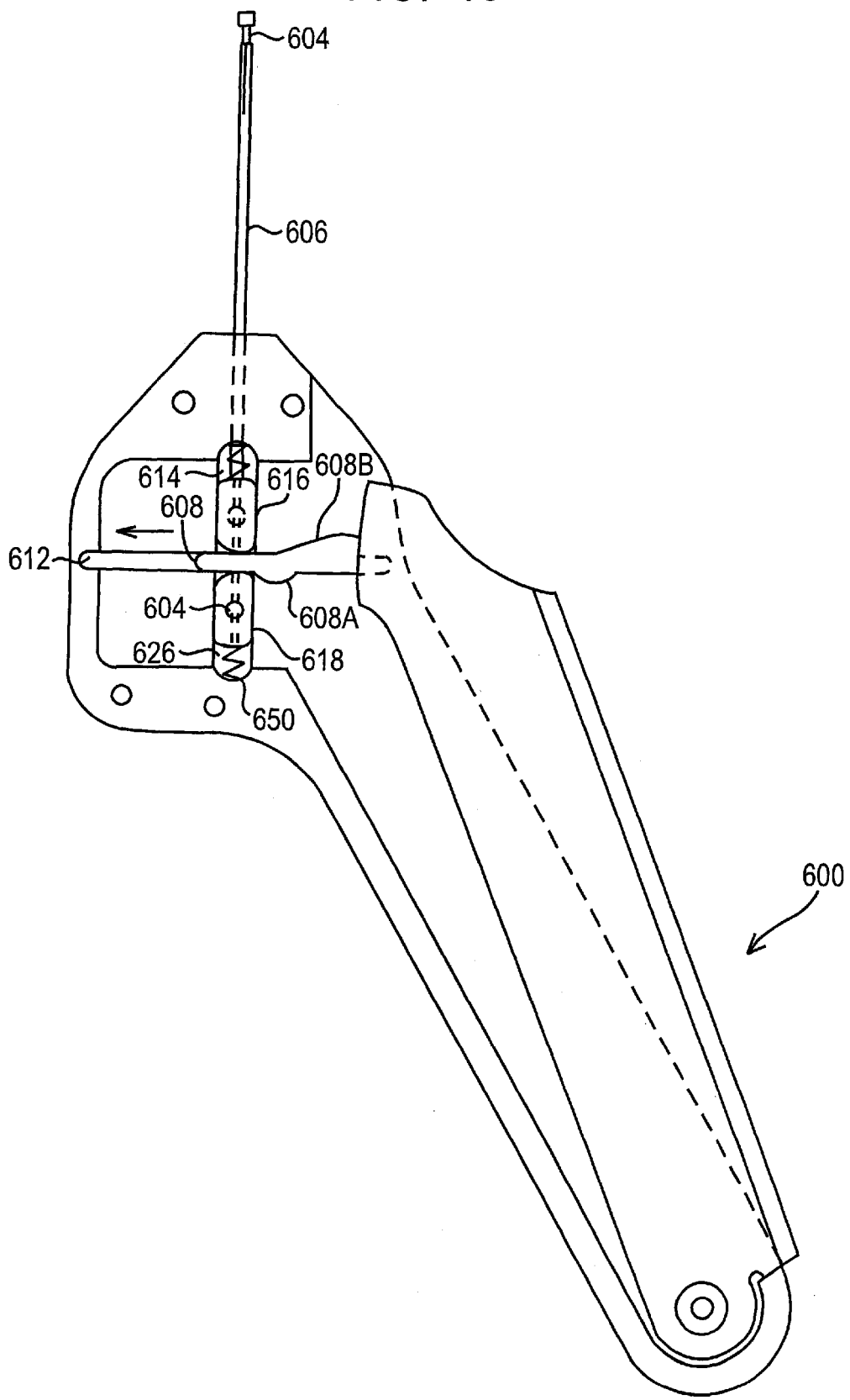
FIGS. 16 and 17 are isometric views of another exemplary staple deployment mechanism of the stapler of the present invention.
Figure 17:
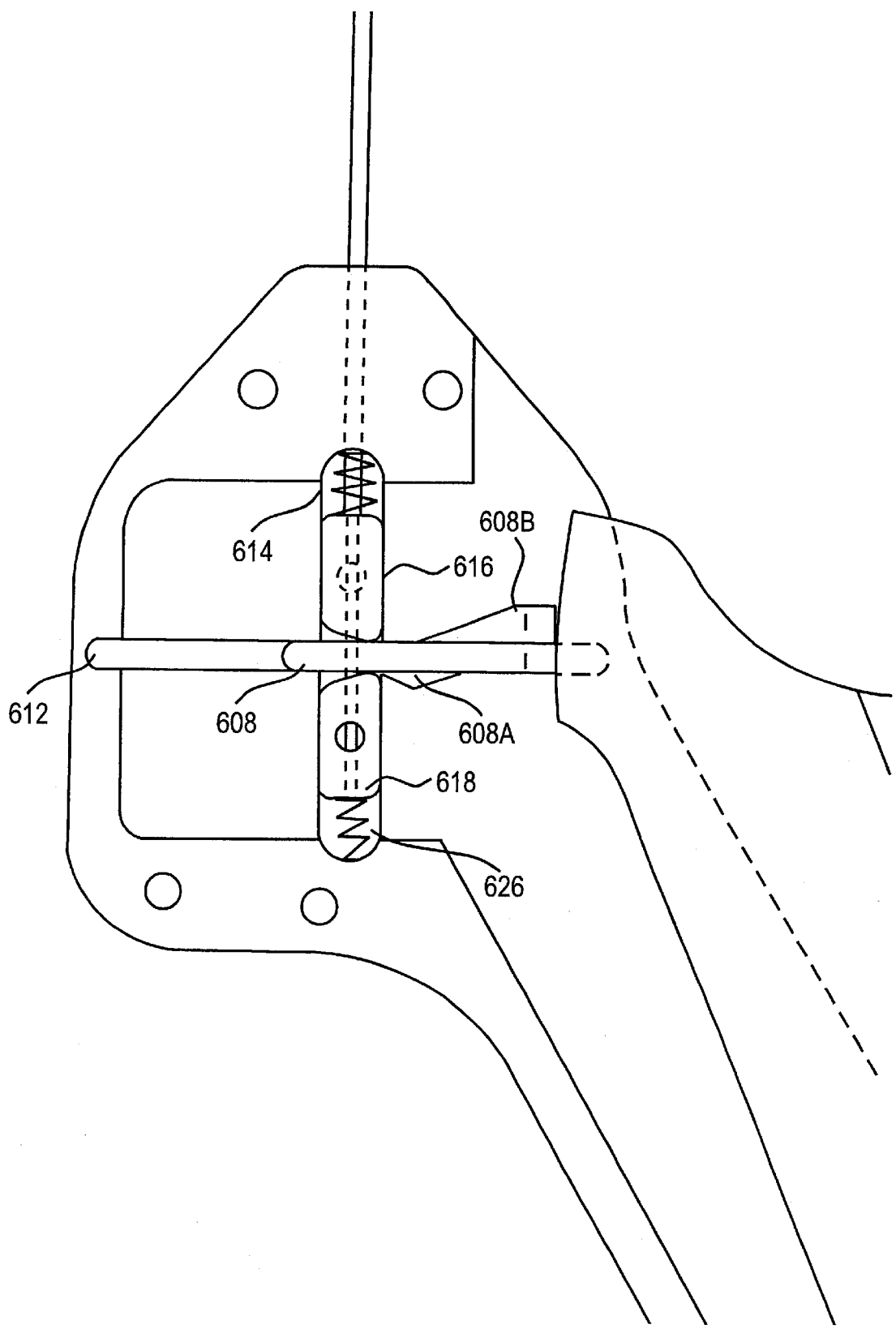

FIGS. 16 and 17 show an alternative cam mechanism. Similar to the previous example, cam 608 is urged in a direction indicated by the arrow to cause relative motion between the mandrel rod and the sleeve. Lobes 608A and 608B are located on opposite sides of cam 608. As the cam 608 is moved along slot 612, the lobe 608A urges a cam follower 618 in a linear motion along a slot 626. This urges the cam follower 618 proximally. The cam follower 618 is coupled to a mandrel rod 604. This deforms staple 10/50 in the second configuration (see FIG. 2 or 5). As the cam 608 is urged further, the cam follower 618 moves distally to stay in contact with the lobe 608A. This urges mandrel rod 604 distally. The same movement of the cam 608 urges lobe 608B to urge cam follower 616 distally. The cam follower 616 is coupled to a sleeve 606. This urges sleeve 606 distally. The downward slope of lobe 608A is parallel with upward slope of lobe 608B so the mandrel rod 604 and the sleeve 606 move distally in unison and the staple is advanced into the tissue. The movement of the cam follower 618 down the slope of lobe 608A then ceases while the movement of cam follower 616 continues up the slope of lobe 608B, the staple 10/50 is deformed into the closed or deployed configuration (see FIG. 3 or 6). Springs 614 and 650 can be provided to return cam followers 616 and 618, respectively, to an initial position. Of course an additional spring can be provided in slot 612 to move cam 608 back to an original position.

Alternatively, the actuation mechanism can include a rotating drum (not shown) to replace the cam 408 and 612. The drum may be adapted with lobes formed thereon, similar to lobes 408A–408C and 608A–608B, respectively. Other alternatives may include a rotating screw having a variable width in accordance with lobes 408A–408C or 608A–608B to actuate the mandrel rod and/or sleeve. Of course, instead of the cam mechanisms depicted in the Figures, direct linkage may be used to actuate the mandrel rod and/or sleeve.

Wound Site Management and Dilator

Figure 18:
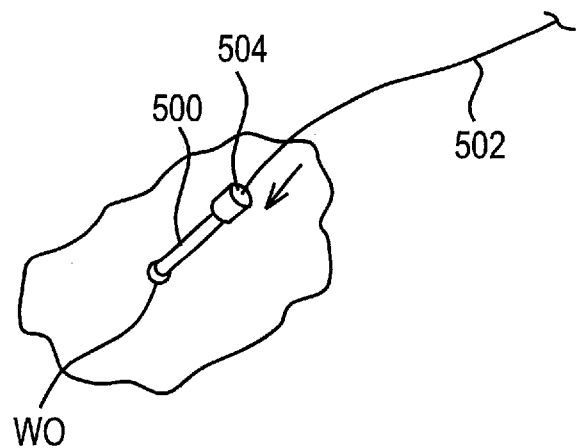
Figure 19:
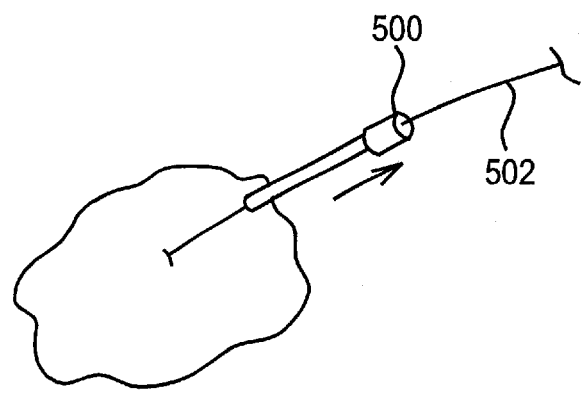

FIGS. 18–25A depict procedural embodiments of wound site management during and after a medical procedure, such as angioplasty. FIG. 18 depicts a conventional tubular dilator 500 extending through the skin of a patient. Typically, the dilator 500 is left in the skin following a completed medical procedure. When the medical procedure has been completed, the wound site must be stabilized. Although the blood flow may not be completely stopped, the blood flow is reduced to a point where the coagulants in the blood can complete the wound closure. To start the stabilization process of the wound site, the doctor inserts a flexible guide wire 502 through an opening 504 in the end of the dilator 500. FIG. 19 shows the step of removing the introducer 500 from the wound site after the guide wire 502 is properly inserted through the skin and into the artery.

Figure 20:
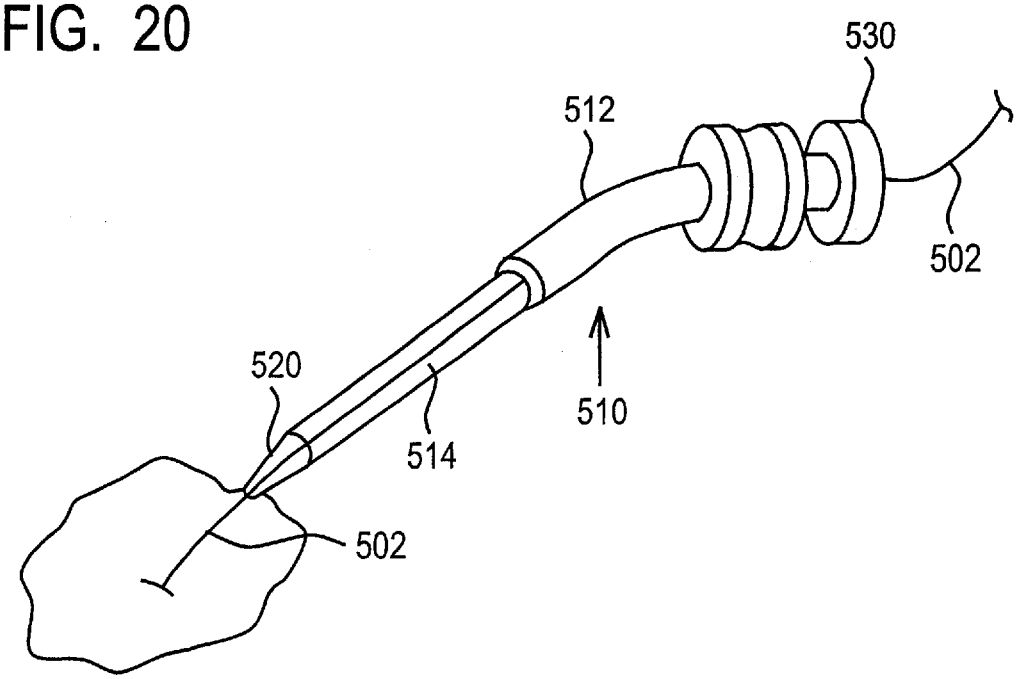

To facilitate efficient wound closure, another aspect of the present invention provides an introducer formed to stretch the wound site for more efficient and effective closure. FIG. 20 depicts the introducer 510 of the present invention, and continues the process from FIGS. 18 and 19 where the introducer 510 slides over the guide wire 502 through an opening in the introducer 510 and a portion of the introducer is placed into the artery. Details of the introducer 510 are disclosed below.

Figure 20A:
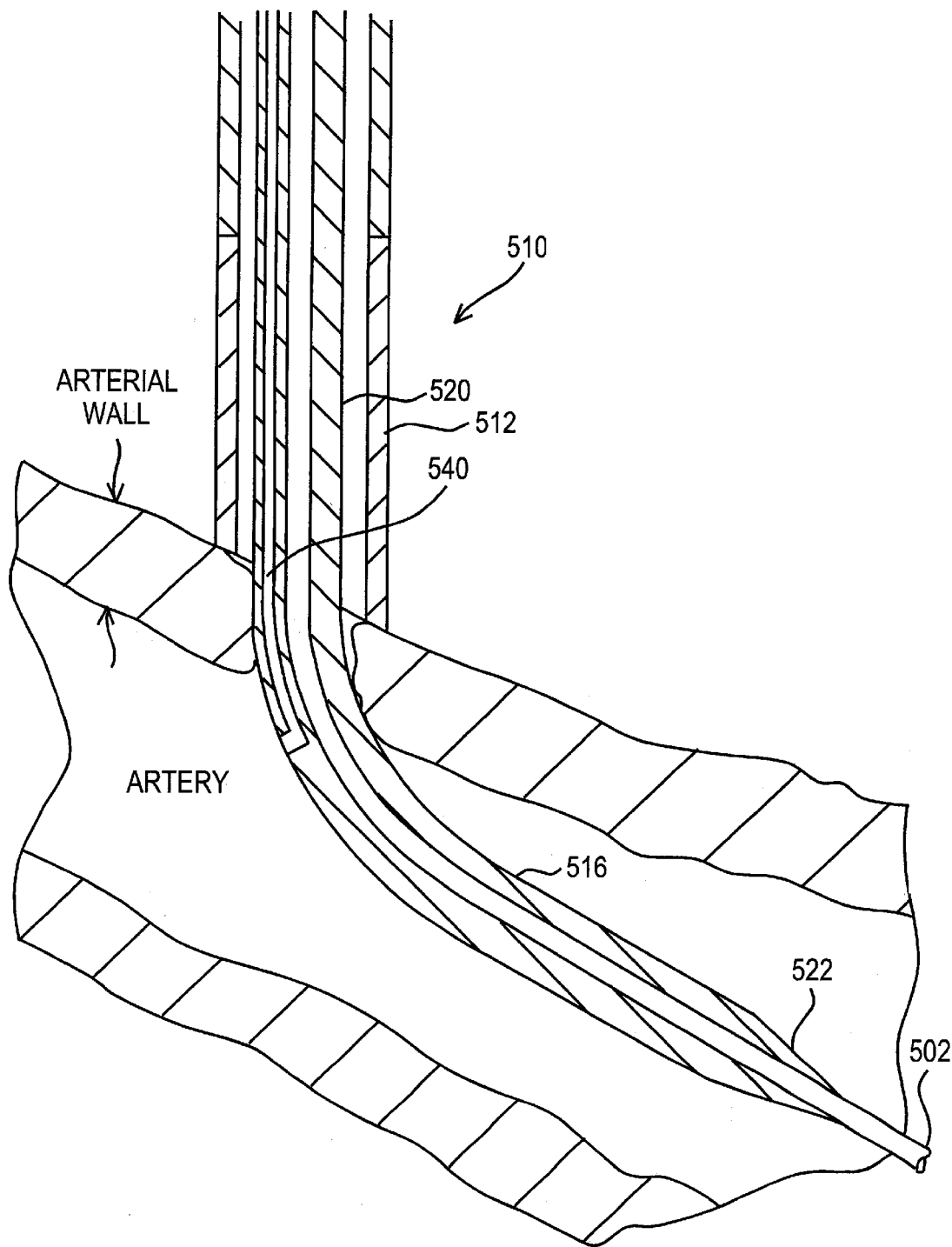
FIG. 20A depicts an exemplary introducer of the present invention.

FIG. 20 depicts the introducer 510 inserted over the guide wire 502 (already in the artery) and inserted into the artery. The introducer includes a hollow elongated guide sheath 512 and dilator 520. Referring to FIG. 20A, the doctor urges the distal tip 516 of the dilator 520 into and through the guide sheath 512 (over guide wire 502). A flexible distal end 516 of the dilator 520 is inserted into the wound, until a blood marker BM indicates that the dilator 520 is properly positioned in the artery. The blood marker BM located at a predetermined length along the dilator 520 allows blood to flow through a cavity 540 to alert the doctor that the dilator 520, and more specifically the flexible distal tip 516, is properly inserted in an artery. Most preferable, the distal tip 516 of the dilator includes a tapered portion 522 to facilitate easier ingress into the artery. An additional blood marking passageway (not shown) can be included on the distal end of sheath 512 as precautionary indicator of the depth of the sheath. Presence of blood in this additional passageway is indicative of the sheath being pressed too far and into the arterial wall or into the artery.

Preferably, the diameter of distal end of the guide sheath 512 can expand if outward pressure is applied from inside surface of the guide sheath 512. More preferably, slits or weakened tear seams (described below) are formed in the distal end of the guide sheath 512 to allow the diameter of the guide sheath to increase when pressure is applied.

Figure 21:
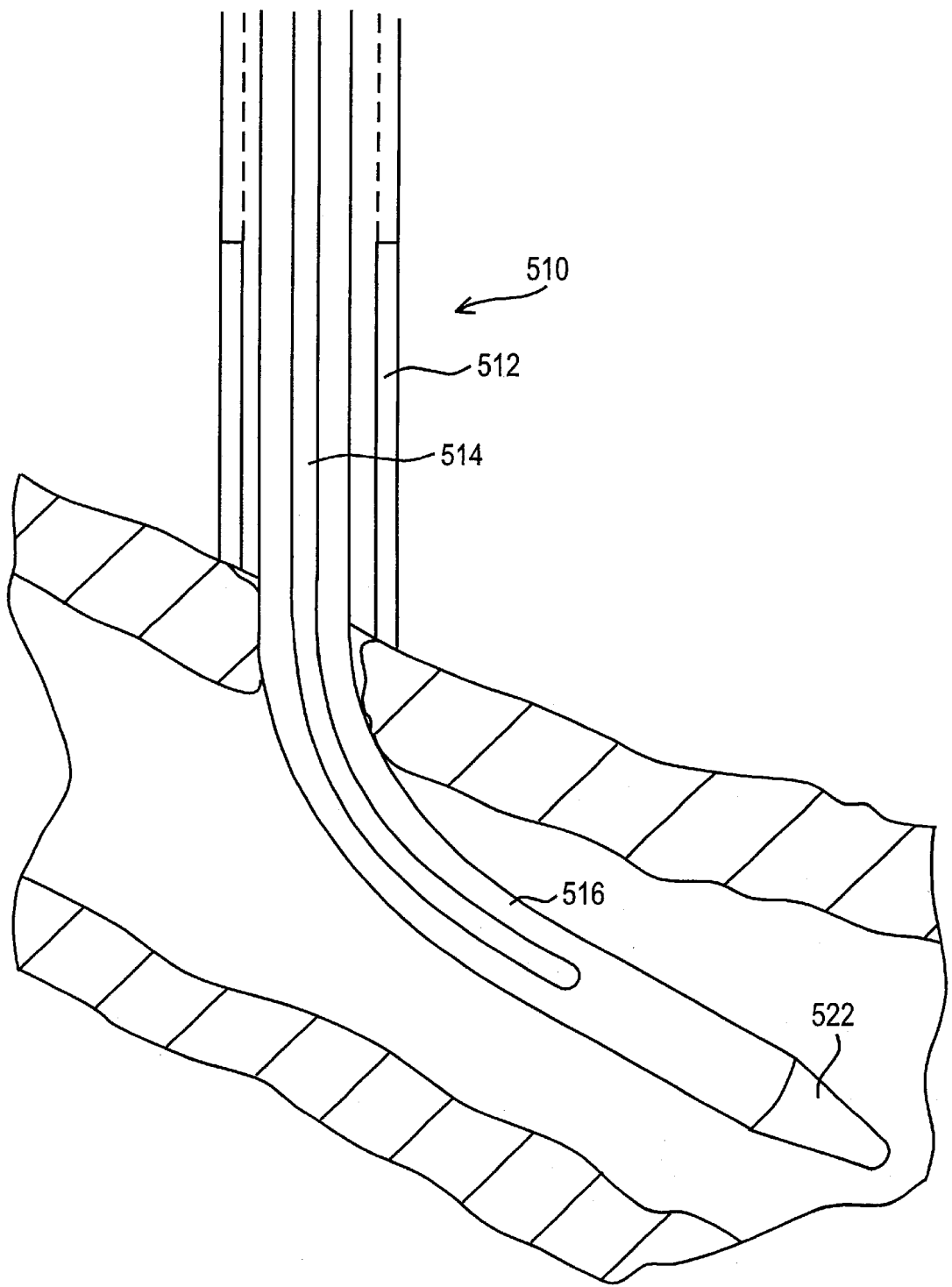
Figure 26:
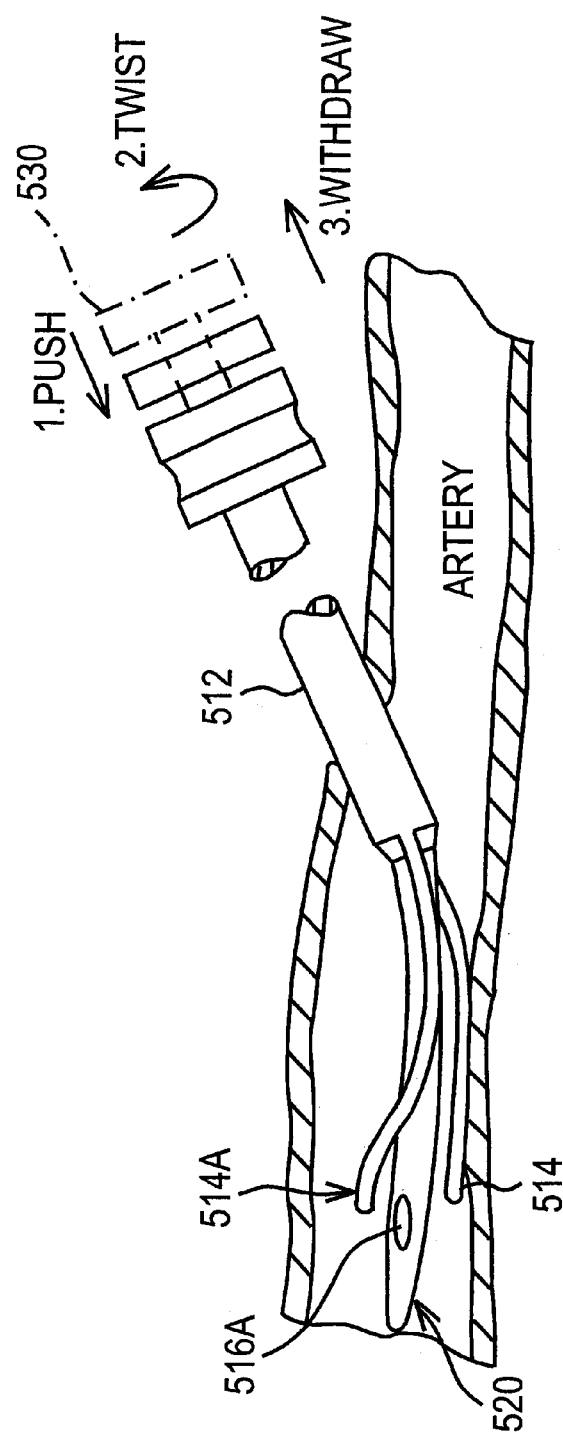

A feature of the guide sheath of the present invention is the use of two or more wire guides to maintain the sheath centered on the wound site, to permit opposing sides of the wound to approximate, and to ensure that the closure device (e.g., stapler/staple, suturing device, cauterization, etc) remains centered about the wound so that wound closure is centered. Preferably, wire guides are formed on opposing sides of the guide sheath 512. The wire guides are delivered into the artery by the dilator 520, as shown in FIGS. 21 and 26. The wire guide 514 are preferably flexible, and removably coupled to the distal end 516 of the dilator 520 and deployed into the wound, as shown in FIG. 26. The wire guides can be held in openings or slots (not shown) on the sides of dilator. Once the dilator is properly inserted into the wound to a proper depth (as indicated by the BM passageway), the dilator is removed from the wound and the guide sheath. To remove the dilator 520 from the guide sheath 512, the doctor first holds the guide sheath 512 and advances the dilator 520 inward (and upward) through the guide sheath 512. This decouples the guide wires 514A and 514B from the openings. To ensure that the guide wires 514A and 514B properly decouple from the dilator 520 before the dilator is withdrawn, a mechanism is provided that does not allow withdrawal until the guide rod has been inserted a predetermined distance. As shown in the drawing this mechanism can include a hub mechanism that requires a twisting motion or other action prior to withdrawal. After the guide rod has been inserted the predetermined distance, the doctor simply extracts the guide rod. This leaves the guide sheath 512 centered on the wound with the guide wires 514A and 514B extending inside the wound.

Figure 23:
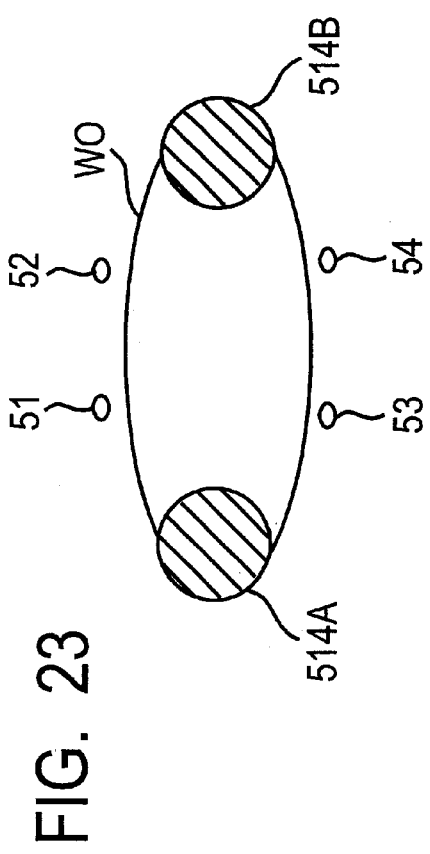

As is understood to those skilled in the diagnostic and interventional arts, a puncture in an artery or vein has a general tendency to manifest a slit or an elongated opening, since the cell structure forming this tissue forms circumferentially (rather than longitudinal) to support radial expansion and contraction of the vessel. The wire guides 514A and 514B of the present invention enable the wound to approximate the natural state of the wound, i.e., elongated circumferentially. Preferably, the sheath has a diameter approximately equal to the diameter of the opening or wound, so that the wire guides 514A and 514B on the sides of the sheath approximate the diameter of the long axis of the wound, as best shown in FIG. 23. Approximation in this sense may mean that the wire guides are less than or greater than (or equal to) this diameter. In effect, the wire guides in this position limit movement of the sheath along the long axis, and since the wound is elongated, movement along the short axis is likewise limited. This ensures that any device inserted through the sheath is approximately centered on the wound.

Importantly, since the wound opening tends to assume the shape shown in FIG. 23 even in the absence of the wire guides, the opposing tissue located along the short axis tends to approximate. The present invention takes advantage of this tendency. If the position of the wire guides define a diameter larger than tissue along the short axis tends to approximate more (i.e., the tissue is stretched along the long axis). However, sufficient wound site management does not require that the wire guides stretch the wound. Rather, if the position of the wire guides are shorter than the wound length, the wire guides still serve to maintain the sheath generally centered at the wound. In both circumstances, the wire guides ensure that a staple deployment is centered, and that a significant amount of tissue is grasped by the staple for closure. Also, if the wound opening in the tissue is held taught by the introducer, there is less tendency for the tissue surrounding the opening to slip down into the vessel during staple deployment (which would reduce the effectiveness of the closure). FIG. 23 also shows examples of locations S1, S2, S3, and S4 of where the prongs of the staple to be inserted will line-up relative to the wound opening WO. The guide wires 514 are preferably disposed on opposing sides of the guide sheath 512, and more preferable, the guide wires are inserted into the wound opening transversally to the long axis of the artery or vein, so that the wound is pulled taught in a transverse direction.

Figures 22, 22A:
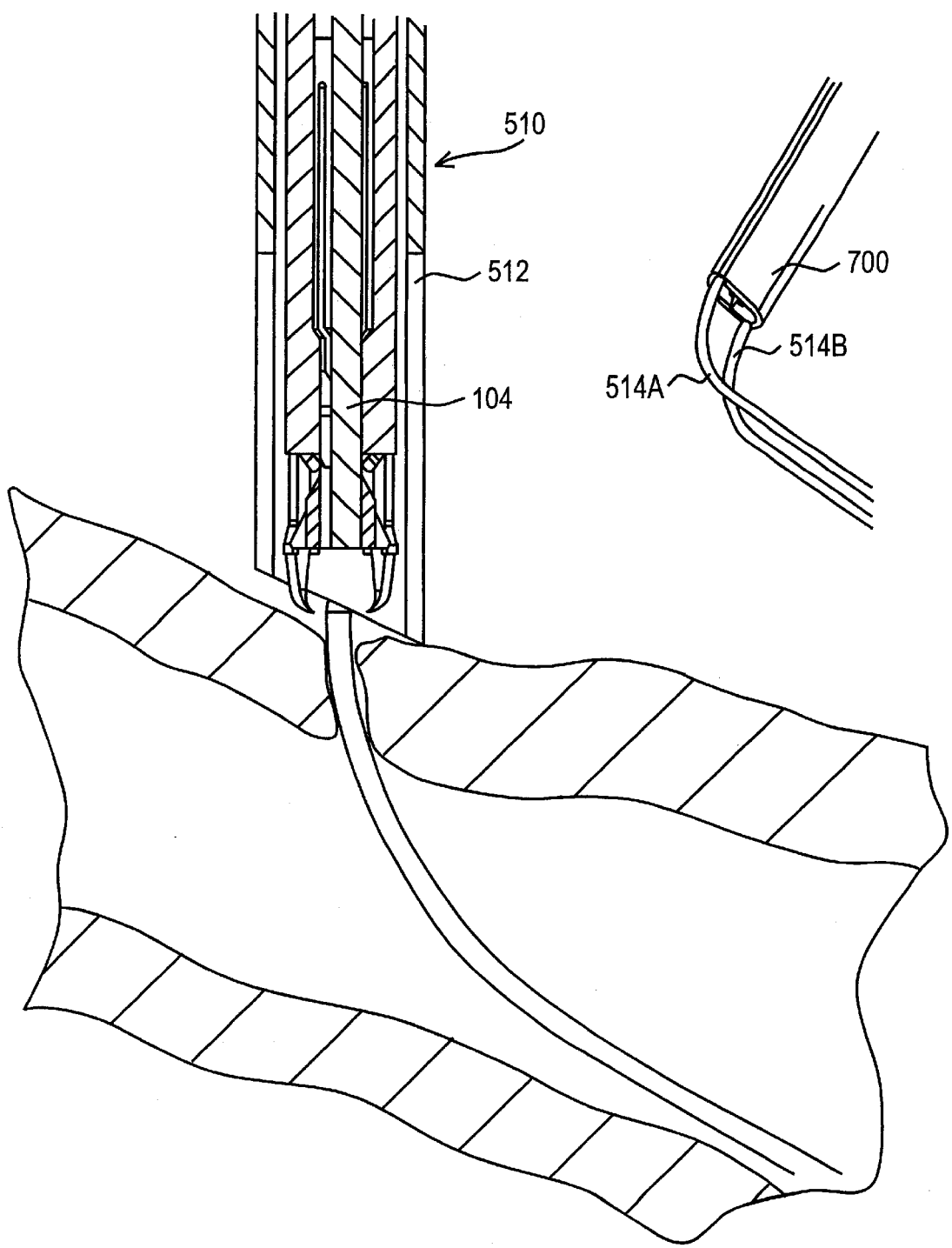
Figures 25, 25A:
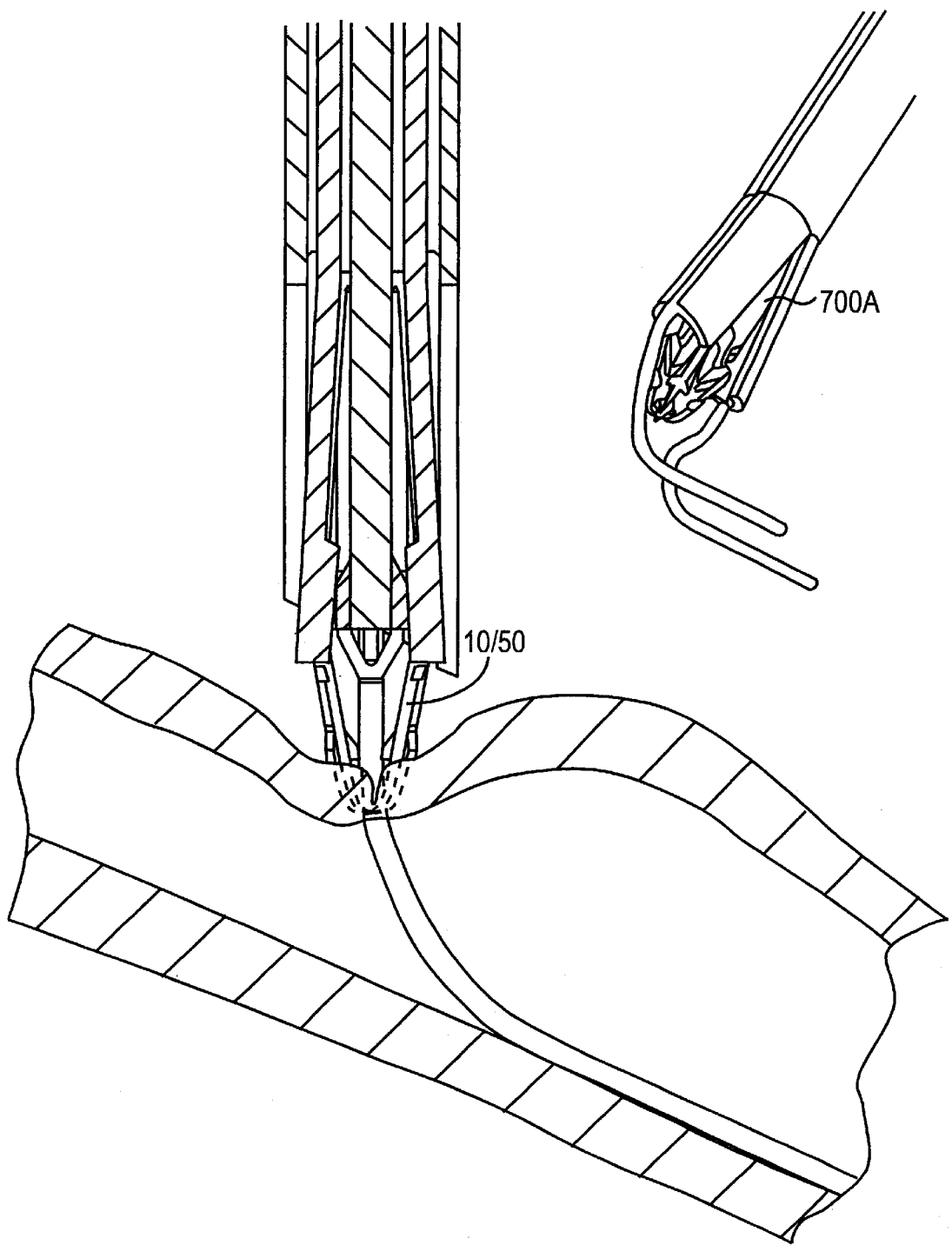

FIG. 22 shows the distal end of a stapler 104 with a staple 10/50 being inserted through the guide sheath 512 of the introducer 510. FIG. 22A depicts a relief view of the introducer 510, and more clearly depicts the slits or weakened tear seams 700. When the distal end of the stapler 104 is properly inserted in the guide sheath 512, the staple can be deployed into the tissue. FIG. 24 shows the first step of staple deployment, the process of which is described in detail above. Note that in FIG. 24A, the extension of the staple prongs causes the weakened tear seam or slits to separate. This further causes the wire guides to expand against the long axis of the wound, thereby further approximating the tissue surrounding the opening. The diameter formed by the prongs of the staple 10/50 is now larger than the original outside diameter of the guide sheath 512. FIGS. 25 and 25A depict the staple fully deployed into tissue, the process of which is described above. The stapler can now be removed from the guide sheath 512. The guide sheath 512 can now be urged away from the wound opening WO and the guide wires 514A and 514B are extracted from the closed opening.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A tissue stapler, comprising
   an elongated sleeve having an inside diameter,
   an elongated rod with a flared mandrel couple to a distal end, the rod and mandrel sized to fit within the inside diameter of the sleeve;
   an actuator mechanism to move the rod relative to the sleeve,
   a staple adapted to fit between said mandrel and said sleeve, and
   said actuator mechanism adapted to move said mandrel relative to said staple and said sleeve causing said staple to close on tissue located about a wound site;
   wherein said mandrel causing at least a portion of said staple to expand before causing said staple to close on said tissue.

2. A tissue stapler as claimed in claim 1, said actuator mechanism comprising a cam for urging said sleeve to move relative to said mandrel.

3. The stapling device of claim 2, further comprising a first cam follower coupled to said sleeve and a second cam follower coupled to said mandrel rod, said cam urging said first and second cam followers to move said sleeve relative to said mandrel.

4. The stapling device of claim 1, wherein said mandrel causes the staple prongs to contract inward thereby deploying said staple into said tissue.

5. A stapler, comprising:
   a distal tip comprising a sleeve and a rod inserted into said sleeve, said rod comprising a flared distal tip;
   an actuator coupled to said sleeve and said rod, said actuator adapted to cause said sleeve to move relative to said rod; and
   a tissue staple comprising a plurality of tissue piercing prongs placed around said rod between said sleeve and said flared distal tip;
   wherein said movement of said sleeve relative to said rod causing said flared distal tip to expand said tissue piercing prongs away from said rod.

6. A stapler as claimed in claim 5, wherein said movement of said sleeve relative to said rod causing said tissue piercing prongs to move together.

7. A process for closing a wound, comprising the steps of:
inserting an introducer into a tissue wound,
placing a sheath around the introducer and locating the sheath approximate to said wound,
inserting the distal end of a stapler into said sheath to approach the tissue wound site, said stapler including a tissue staple on the distal end of said stapler,
expanding a portion of the staple about said wound, and
contracting at least a portion of said staple pulling the tissue surrounding the wound together.

8. A process for closing a wound in an artery with a staple, comprising the steps of:
inserting an introducer with a plurality of guide wires coupled thereto into an artery,
guiding a stapler and staple to the wound site,
expanding said staple to surround said wound site before entering said tissue, and
closing said staple on said tissue to close said wound.

* * * * *